US008431727B2

(12) United States Patent
Bonrath et al.

(10) Patent No.: US 8,431,727 B2
(45) Date of Patent: *Apr. 30, 2013

(54) PROCESS FOR THE MANUFACTURE OF CHROMAN DERIVATIVES, ESPECIALLY α-TOCOPHEROL AND ALKA-NOATES THEREOF

(75) Inventors: Werner Bonrath, Freiburg (DE); Yann Foricher, Riedisheim (FR); Thomas Netscher, Bad Krozingen (DE); Angela Wildermann, Bad Säckingen (DE)

(73) Assignee: DSM Assets B.V., Heerlen (NL)

( * ) Notice: Subject to any disclaimer, the term of this patent is extended or adjusted under 35 U.S.C. 154(b) by 815 days.

This patent is subject to a terminal disclaimer.

(21) Appl. No.: 12/381,127

(22) Filed: Mar. 6, 2009

(65) Prior Publication Data

US 2009/0176998 A1  Jul. 9, 2009

Related U.S. Application Data

(63) Continuation of application No. 11/005,113, filed on Dec. 6, 2004, now abandoned.

(30) Foreign Application Priority Data

Jun. 11, 2004 (EP) .................................... 04013713

(51) Int. Cl.
*C07D 311/00* (2006.01)
*B01J 27/06* (2006.01)
*B01J 27/135* (2006.01)

(52) U.S. Cl.
USPC ............ 549/411; 502/224; 502/226; 502/227

(58) Field of Classification Search .................. 549/411; 502/224, 226, 227
See application file for complete search history.

(56) References Cited

U.S. PATENT DOCUMENTS

| | | | |
|---|---|---|---|
| 2,411,967 A | 12/1946 | Karrer et al. | |
| 3,708,505 A | 1/1973 | Greenbaum et al. | |
| 3,789,086 A | 1/1974 | Frick et al. | |
| 4,191,692 A | 3/1980 | Grafen et al. | |
| 5,663,376 A | 9/1997 | Hirose et al. | |
| 7,696,364 B2 * | 4/2010 | Bonrath et al. | ............... 549/411 |
| 2005/0171362 A1 | 8/2005 | Bonrath et al. | |

FOREIGN PATENT DOCUMENTS

| | | |
|---|---|---|
| DE | 2 160 103 | 8/1972 |
| DE | 26 06 830 | 9/1977 |
| DE | 196 54 038 | 6/1998 |
| EP | 0 100 471 | 2/1984 |
| EP | 0 694 541 | 1/1996 |
| JP | 56-073081 | 6/1981 |

OTHER PUBLICATIONS

Frost et al., "Indium Triflate: An Efficient Catalyst for Friedel-Crafts Acylation of Aromatics," Fourth International Electronic Conference on Synthetic Organic Chemistry, Sep. 1-30 (2000).
Matsui, M. et al., "Synthesis of -TocopherolScandium (III) Trifluoromethanesulfonate as an Efficient Catalyst in the Reaction of Hydroquinone with Allylic Alcohol," Bull. Chem. Soc. Jpn. 68, pp. 3569-3571 (1995).
Ullman's Encylcopedia of Industrial Chemistry, vol. A27, 5th Edition, pp. 484-485 (1996).
Derwent English language abstract of DE 196 54 038, Jun. 25, 1998.
Derwent English language abstract of DE 26 06 830, Sep. 8, 1977.
JAPIO English language abstract of JP 56073081, Jun. 17, 1981.

* cited by examiner

*Primary Examiner* — Andrew D Kosar
*Assistant Examiner* — Raymond Covington
(74) *Attorney, Agent, or Firm* — Baker Donelson Bearman Caldwell & Berkowitz, PC

(57) ABSTRACT

The present invention relates to novel processes for the manufacture of chroman derivatives such as α-tocopherol (TCP) and alkanoates thereof, especially α-tocopheryl acetate (TCPA), whereby at least one step of the processes is carried out in the presence of a Lewis acid or a mixture of a Lewis acid with a Bronsted acid as the catalyst under pressure, preferably at an absolute pressure of at least 1.1 bar.
As starting materials for the manufacture of TCP and its alkanoates either a mixture of 2,3,5-trimethylhydroquinone (TMHQ) or 2,3,6-trimethylhydroquinone-1-alkanoate (TMHQA) and a compound selected from the group consisting of phytol (PH), isophytol (IP) and (iso)phytol derivatives or 2-phytyl-3,5,6-trimethyl-hydroquinone (PTMHQ)/3-phytyl-2,5,6-trimethylhydroquinone-1-alkanoate (PTMHQA) and/or an isomer thereof are used.
Suitable Lewis acids are indium(III) salts and scandium(III) salts. Suitable acid mixtures are iron/iron(II) chloride/hydrogen chloride and zinc(II) chloride/hydrogen chloride.

22 Claims, No Drawings

PROCESS FOR THE MANUFACTURE OF CHROMAN DERIVATIVES, ESPECIALLY α-TOCOPHEROL AND ALKA-NOATES THEREOF

This application is a continuation of U.S. patent application Ser. No. 11/005,113, filed Dec. 6, 2004, now abandoned which claims priority to European Patent Application No. 04013713.5, filed Jun. 11, 2004.

The present invention relates to a novel process for the manufacture of chroman derivatives, especially for the manufacture of α-tocopherol (TCP) and alkanoates (TCPA) thereof such as α-tocopheryl acetate (TCPAc), whereby at least one step of the process is carried out in the presence of a Lewis acid or a mixture of a Lewis acid with a Bronsted acid as the catalyst under pressure. Preferably the absolute pressure of the reaction is at least 1.1 bar, more preferably it is from about 1.1 bar to about 20.0 bar, even more preferably it is from about 1.1 bar to about 6.0 bar.

As starting materials for the manufacture of TCP and its alkanoates either a mixture of 2,3,5-trimethylhydroquinone (TMHQ) or 2,3,6-trimethylhydroquinone-1-alkanoate (TMHQA) and a compound selected from the group consisting of phytol (PH), isophytol (IP) and (iso)phytol derivatives, or the "open ring" compound 2-phytyl-3,5,6-trimethyl-hydroquinone (PTMHQ), a 3-phytyl-2,5,6-trimethylhydroquinone-1-alkanoate (PTMHQA) and/or an isomer thereof are used.

As is known, (all-rac)-α-tocopherol (or as it has mostly been denoted in the prior art, "d,1-α-tocopherol") is a mixture of four diastereomeric pairs of enantiomers of 2,5,7,8-tetramethyl-2-(4',8',12'-trimethyl-tridecyl)-6-chromanol (α-tocopherol), which is the biologically most active and industrially most important member of the vitamin E group.

Many processes for the manufacture of "d,1-α-tocopherol" (referred to as such in the literature reviewed hereinafter) and its acetate by the reaction of TMHQ/2,3,6-trimethyl-hydroquinone-1-acetate (TMHQAc) with IP or PH in the presence of a catalyst or catalyst system and in a solvent or solvent system are described in the following selected literature.

The manufacture of α-tocopherol by the reaction of TMHQ with PH or phytyl bromide in the presence of anhydrous $ZnCl_2$ is e.g. described in U.S. Pat. No. 2,411,967. According to DE 196 54 038 A1 TMHQ is reacted with PH or IP to α-tocopherol and its acetate in the presence of $ZnCl_2$ and a proton donor, whereby in the process of U.S. Pat. No. 3,708,505 a combined acid condensation agent comprising a Lewis acid such as $ZnCl_2$ and at least one strong acid such as p-toluene sulfonic acid and sodium bisulfate is used as the catalyst.

In EP-A 0 100 471 the reaction of TMHQ with IP or PH in the presence of a Lewis acid, e.g. $ZnCl_2$, $BF_3$ or $AlCl_3$, a strong acid, e.g. HCl, and an amine salt as the catalyst system is described. In the processes of DE-OS 26 06 830 and U.S. Pat. No. 4,191,692 the IP or PH is pretreated with ammonia or an amine before the reaction with TMHQ in the presence of $ZnCl_2$ and an acid is effected.

In the processes of DE-OS 21 60 103 as well as U.S. Pat. No. 3,789,086 compounds of the following formula

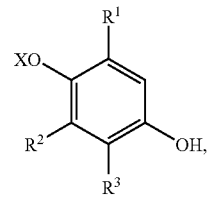

wherein X is hydrogen, alkanoyl or aroyl, and $R^1$, $R^2$ and $R^3$ are individually hydrogen or methyl, are reacted with compounds of the following formulae

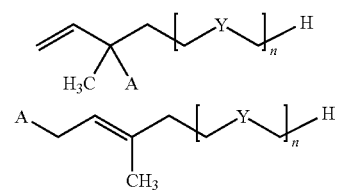

wherein Y is —$CH_2$—CH($CH_3$)— or —CH=C($CH_3$)— and A is halogen, hydroxy, etherified hydroxy or esterified hydroxy in the presence of HCl and Fe and/or $FeCl_2$ as the catalyst to obtain e.g. α-tocopherol.

According to EP-A 0 694 541 TMHQ and IP, PH or a PH derivative are reacted in the presence of a mineral acid, a Lewis acid, an acidic ion exchange resin or a triflate, nitrate or sulfate of Sc, Y or a lanthanide element as the catalyst. The use of Sc(III) triflate as catalyst for the condensation of TMHQ with IP is also described in Bull. Chem. Soc. Jpn. 1995, 68, 3569-3571.

TCP can be converted into its acetate, succinate and further known application forms by standard methods, e.g. as described in Ullmann's Encyclopedia of Industrial Chemistry, Vol. A27, 5$^{th}$ edition, pages 484 to 485, VCH Verlagsgesellschaft mbH, D-69451 Weinheim, 1996. In contrast to TCP which is labile against oxidative conditions, the esters (TCPA) are more stable and more convenient to handle.

The object of the present invention is to provide a process for the manufacture of chroman derivatives such as tocols and tocopherols and of their alkanoates, especially of α-tocopherol and its alkanoates, with high selectivities and yields.

According to the present invention this object is achieved by the use of a Lewis acid or a mixture of a Lewis acid with a Bronsted acid as the catalyst under pressure, preferably at an absolute pressure of at least 1.1 bar, more preferably at an absolute pressure of from about 1.1 bar to about 20.0 bar, even more preferably at an absolute pressure of from about 1.1 bar to about 6.0 bar. It has been surprisingly found that pressure has a positive effect on the condensation reaction of phenols such as TMHQ or TMHQA with compounds such as IP, PH or a derivative thereof and on the ring closure reaction of PTMHQ or PTMHQA and/or isomers thereof to produce α-tocopherol as well as on the acylation of tocols and tocopherols.

Therefore, in one aspect, the present invention is concerned with a process for the manufacture of 2-alkenyl-3,5,6-trimethylhydroquinone (formula I with n=0 to 3; $R^1$=hydrogen) and 3-alkenyl-2,5,6-trimethylhydroquinone 1-alkanoate (formula I with n=0 to 3; $R^1$=acetyl, propionyl, pivaloyl, $HO_2C$—

$CH_2$—$CH_2$—CO, nicotinoyl or benzoyl), most preferably a process for the manufacture of 2-phytyl-3,5,6-trimethylhydroquinone (formula I with $R^1$=hydrogen and n=3) and 3-phytyl-2,5,6-trimethylhydroquinone-1-alkanoates (formula I with $R^1$=acetyl, propionyl, pivaloyl, $HO_2C$—$CH_2$—$CH_2$—CO, nicotinoyl or benzoyl and n=3),

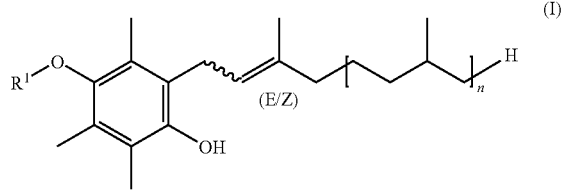

by reacting 2,3,5-trimethylhydroquinone (formula II with $R^1$=hydrogen) and 2,3,6-trimethylhydroquinone-1-alkanoate (formula II with $R^1$=acetyl, propionyl, pivaloyl, $HO_2C$—$CH_2$—$CH_2$—CO, nicotinoyl or benzoyl), respectively,

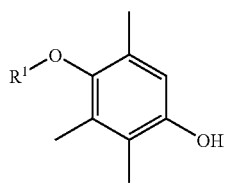

with a compound of the formula III and/or IV in an organic solvent

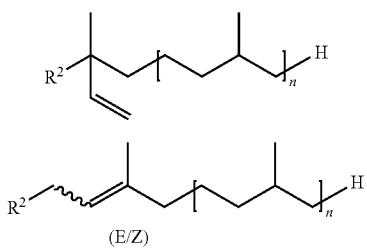

whereby $R^1$ is hydrogen, acetyl, propionyl, pivaloyl, $HO_2C$—$CH_2$—$CH_2$—CO, nicotinoyl or benzoyl,
$R^2$ is hydroxy, acetyloxy, benzoyloxy or halogen, and
n is an integer from 0 to 3, and
whereby the reaction is carried out in the presence of a Lewis acid or a mixture of a Lewis acid with a Bronsted acid as the catalyst under pressure, preferably at an absolute pressure of at least 1.1 bar, more preferably at an absolute pressure of from about 1.1 bar to about 20.0 bar, even more preferably at an absolute pressure of from about 1.1 bar to about 6.0 bar. This process is referred to as PROCESS 1 hereinafter.

Concerning the substituent $R^1$: preferably it is hydrogen or acetyl, more preferably it is hydrogen.

Concerning the substituent $R^2$: preferably $R^2$ is hydroxy, acetyloxy, benzoyloxy, chlorine or bromine, more preferably $R^2$ is hydroxy, acetyloxy or chlorine, most preferably $R^2$ is hydroxy.

Concerning the integer n: preferably n is 3.

While in PROCESS 1 of the present invention the production of (all-rac)-2-alkenyl-3,5,6-trimethylhydroquinone, e.g. (all-rac)-PTMHQ, or (all-rac)-3-alkenyl-2,5,6-trimethylhydroquinone 1-alkanoate, e.g. (all-rac)-PTMHQA, especially (all-rac)-3-phytyl-2,5,6-trimethylhydroquinone-1-acetate (PTMHQAc), is preferred, the invention is not limited to the production of that particular isomeric form and other isomeric forms can be obtained by using e.g. phytol (formula IV with $R^2$=OH and n=3), isophytol (formula III with $R^2$=OH and n=3) or a derivative thereof as the starting material in the appropriate isomeric form. Thus, (R,R)-PTMHQ or (R,R)-PTMHQA will be obtained e.g. when using (R,R)-phytol, (R,R,R)-isophytol, (S,R,R)-isophytol or (RS,R,R)-isophytol or an appropriate (iso)phytol derivative.

PROCESS 1 is also applicable for the alkenylation of phenols comprising 0 to 4 methyl groups, a total of 1 to 3 hydroxy groups and at least one unsubstituted position, whereby the unsubstituted position is ortho to a hydroxy group.

Therefore, a further object of the present invention is a process for the alkenylation of phenols comprising 0 to 4 methyl groups, a total of 1 to 3 hydroxy groups and at least one unsubstituted position, whereby the unsubstituted position is ortho to a hydroxy group, with a compound of the formula III and/or IV in an organic solvent

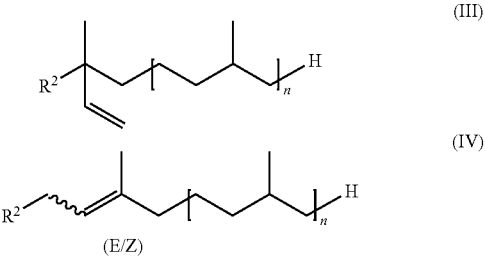

with $R^2$ and n having the same meanings and preferences as above, and
whereby the reaction is carried out in the presence of a Lewis acid or a mixture of a Lewis acid with a Bronsted acid as the catalyst under pressure, preferably at an absolute pressure of at least 1.1 bar, more preferably at an absolute pressure of from about 1.1 bar to about 20.0 bar, even more preferably at an absolute pressure of from about 1.1 bar to about 6.0 bar. This process is referred to as PROCESS 1A hereinafter.

Concerning the Phenols Used in Process 1A as the Starting Material:

Especially suitable phenols have the following formula IIa

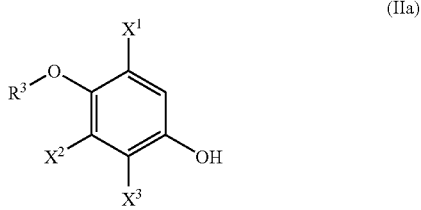

with $R^3$ being hydrogen, acetyl, propionyl, pivaloyl, $HO_2C$—$CH_2$—$CH_2$—CO, nicotinoyl or benzoyl, and $X^1$, $X^2$ and $X^3$ being independently from each other hydrogen or methyl, with the proviso that $R^3$ is only acetyl, propionyl, pivaloyl, $HO_2C$—$CH_2$—$CH_2$—CO, nicotinoyl or benzoyl, if $X^1$, $X^2$ and $X^3$ are all methyl; i.e. hydroquinone, 2-methylhydroquinone, 2,3-dimethylhydroquinone, 2,5-dimethylhydroquinone, 2,6-dimethylhydroquinone, 2,3,5-trimethylhydroquinone and 2,3,6-trimethylhydroquinone-1-alkanoates. Preferred from this group are 2,3,5-trimethylhydroquinone and 2,3,6-trimethylhydroquinone-1-alkanoates, more preferred are 2,3,5-trimethylhydroquinone and 2,3,6-trimethylhydroquinone-1-acetate, the most preferred is 2,3,5-trimethylhydroquinone.

In another aspect, the present invention is concerned with a process for the manufacture of compounds of the formula VII, preferably α-tocopherol (formula VII with $R^1$=hydrogen and n=3) and its alkanoates (formula VII with $R^1$=acetyl, propionyl, pivaloyl, $HO_2$—$CH_2$—$CH_2$—CO, nicotinoyl or benzoyl and n=3)

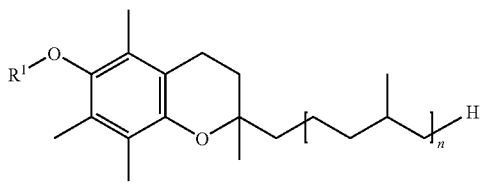

(VII)

by
a) (STEP a) optionally reacting 2,3,5-trimethylhydroquinone (formula II with $R^1$=hydrogen) and 2,3,6-trimethylhydroquinone 1-alkanoate (formula II with $R^1$=acetyl, propionyl, pivaloyl, $HO_2C$—$CH_2$—$CH_2$—CO, nicotinoyl or benzoyl), respectively,

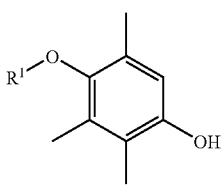

(II)

with a compound of the formula III and/or IV in an organic solvent

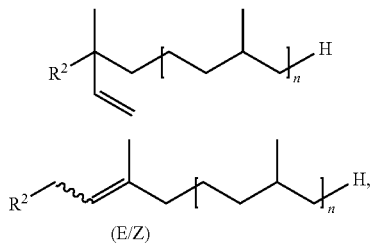

(III)

(IV)

with $R^1$, $R^2$ and n having the same meanings and preferences as above, and
b) (STEP b) submitting in an organic solvent a 2-alkenyl-3,5,6-trimethylhydroquinone (formula I with $R^1$=hydrogen), preferably 2-phytyl-3,5,6-trimethylhydroquinone (formula I with $R^1$=hydrogen and n=3), a 3-alkenyl-2,5,6-trimethylhydroquinone 1-alkanoate (formula I with $R^1$=acetyl, propionyl, pivaloyl, $HO_2C$—$CH_2$—$CH_2$—CO, nicotinoyl or benzoyl), preferably 3-phytyl-2,5,6-trimethylhydroquinone 1-alkanoate (formula I with $R^1$=acetyl, propionyl, pivaloyl, $HO_2C$—$CH_2$—$CH_2$—CO, nicotinoyl or benzoyl and n=3) and optionally one or more double bond isomers thereof, all obtainable by step a),

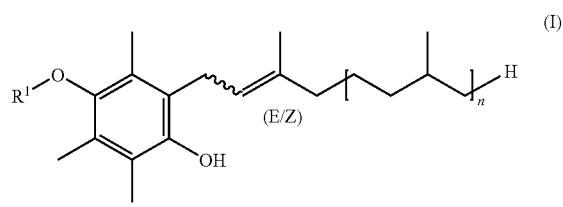

(I)

to ring closure to form chroman derivatives VII, preferably α-tocopherol (formula VII with $R^1$=hydrogen and n=3) or its alkanoate (formula VII with $R^1$=acetyl, propionyl, pivaloyl, $HO_2C$—$CH_2$—$CH_2$—CO, nicotinoyl or benzoyl and n=3),
whereby at least one of the steps a) and b) is carried out in the presence of a Lewis acid or a mixture of a Lewis acid with a Bronsted acid as the catalyst under pressure, preferably at an absolute pressure of at least 1.1 bar, more preferably at an absolute pressure of from about 1.1 bar to about 20.0 bar, even more preferably at an absolute pressure of from about 1.1 bar to about 6.0 bar. This process is referred to in the following as PROCESS 2.

Depending on the activity of the catalyst and the reaction conditions, the reaction of compounds of the formula II with compounds of the formula III and/or IV proceeds to the final product of the formula VII, preferably α-tocopherol and its alkanoate, so that the compounds of the formula I such as PTMHQ (formula I with $R^1$=hydrogen and n=3) and PTMHQA (formula I with $R^1$=acetyl, propionyl, pivaloyl, $HO_2C$—$CH_2$—$CH_2$—CO, nicotinoyl or benzoyl and n=3) are not isolated.

Therefore, a further aspect of the present invention is the manufacture of chroman derivatives VII such as α-tocopherol (formula VII with $R^1$=hydrogen and n=3) and its alkanoates (formula VII with $R^1$=acetyl, propionyl, pivaloyl, $HO_2C$—$CH_2$—$CH_2$—CO, nicotinoyl or benzoyl and n=3)

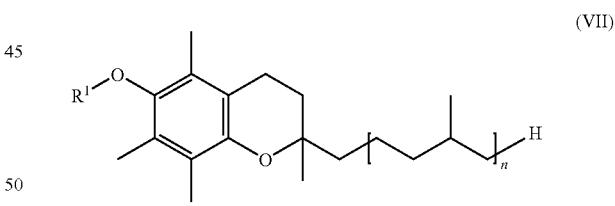

(VII)

by reacting 2,3,5-trimethylhydroquinone (formula II with $R^1$=hydrogen) and 2,3,6-trimethylhydroquinone 1-alkanoate (formula II with $R^1$=acetyl, propionyl, pivaloyl, $HO_2C$—$CH_2$—$CH_2$—CO, nicotinoyl or benzoyl), respectively,

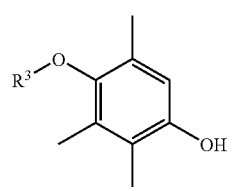

(II)

with a compound of the formula III and/or a IV in an organic solvent

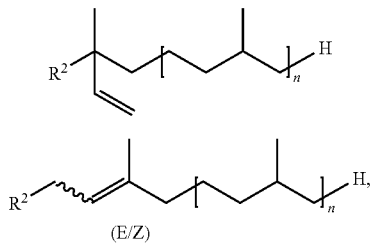

with $R^1$, $R^2$ and n having the same meanings and preferences as above, whereby the reaction is carried out in the presence of a Lewis acid or a mixture of a Lewis acid with a Bronsted acid as the catalyst under pressure, preferably at an absolute pressure of at least 1.1 bar, more preferably at an absolute pressure of from about 1.1 bar to about 20.0 bar, even more preferably at an absolute pressure of from about 1.1 bar to about 6.0 bar. This process is referred to in the following as PROCESS 3.

As starting material in PROCESS 3 also a compound of the formula IX instead of a compound of the formula III and/or IV

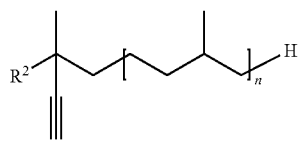

may be used, so that compounds of the formula X

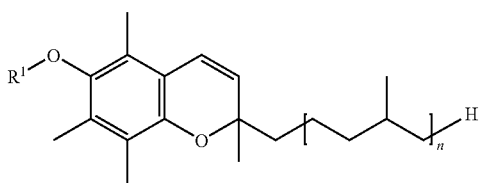

are obtained. $R^1$, $R^2$ and n have the same meanings and preferences as above. To this process it will be referred to in the following as PROCESS 4.

While in the PROCESSES 2 and 3 of the present invention the production of (all-rac)-chroman derivatives such as (all-rac)-TCP (formula VII with $R^1$=hydrogen and n=3) and (all-rac)-TCPA (formula VII with $R^1$=acetyl, propionyl, pivaloyl, $HO_2C$—$CH_2$—$CH_2$—CO, nicotinoyl or benzoyl and n=3), especially (all-rac)-TCPAc (formula VII with R=acetyl and n=3), is preferred, the invention is not limited to the production of that particular isomeric form and other isomeric forms can be obtained by using e.g. phytol, isophytol or a derivative thereof as the starting material in the appropriate isomeric form. Thus, e.g. (RS,R,R)-TCP/(RS,R,R)-TCPA will be obtained when using (R,R)-PTMHQ, (R,R)-PTMHQA, (R,R)-phytol, (R,R,R)-isophytol, (S,R,R)-isophytol or (RS, R,R)-isophytol or an appropriate (iso)phytol derivative.

In an especially preferred embodiment of the invention TMHQ is reacted with PH (formula IV with $R^2$=OH and n=3) and/or IP (formula III with $R^2$=OH and n=3), preferably with IP, to α-tocopherol (formula VII with $R^1$=hydrogen and n=3), whereby as intermediates compounds of the formula V (see below) and VI (see below) such as 2-phytyl-3,5,6-trimethylhydroquinone (formula I with $R^1$=hydrogen and n=3; as main component), 2-(3,7,11,15-tetramethyl-hexadec-3-enyl)-3,5,6-trimethylhydroquinone (formula Va with $R^1$=hydrogen) and 2-[3-(4,8,12-trimethyl-tridecyl)-but-3-enyl]-3,5,6-trimethylhydroquinone (formula VIa with $R^1$=hydrogen) are formed.

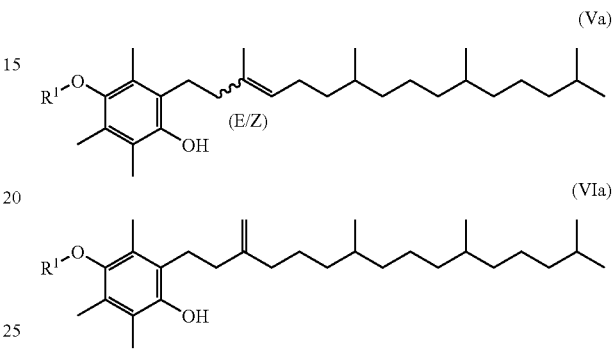

PROCESSES 2 and 3 can also be carried out by using phenols of the formula IIa, whereby, beside α-tocopherol and its alkanoates, e.g. other tocols (formula VIIa with n=3) and tocopherols (formula VIIa with n=3) can be obtained.

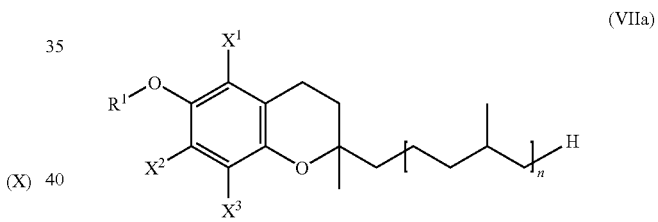

Therefore, in another aspect, the present invention is concerned with a process for the manufacture of compounds of the formula VIIa by a) (STEP a) optionally reacting a compound of the formula IIa

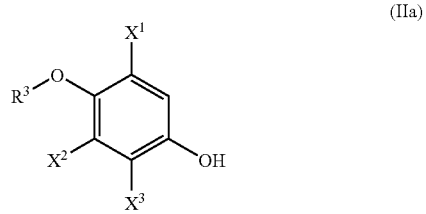

with a compound of the formula III and/or IV in an organic solvent

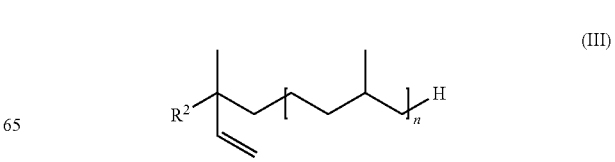

-continued

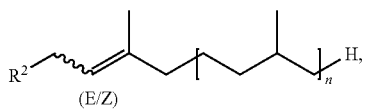
(E/Z)

with $R^2$, $R^3$, n, $X^1$, $X^2$ and $X^3$ having the same meanings and preferences as above, and b) (STEP b) submitting in an organic solvent a compound of the formula Ia and optionally one or more double bond isomers thereof, all obtainable by step a), to ring closure to form a compound of the formula VIIa,

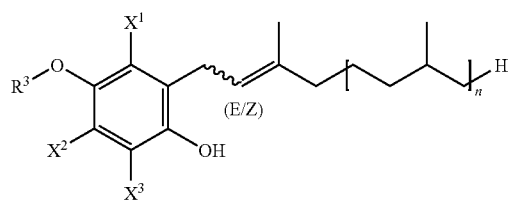

whereby at least one of the steps a) and b) is carried out in the presence of a Lewis acid or a mixture of a Lewis acid with a Bronsted acid as the catalyst under pressure, preferably at an absolute pressure of at least 1.1 bar, more preferably at an absolute pressure of from about 1.1 bar to about 20.0 bar, even more preferably at an absolute pressure of from about 1.1 bar to about 6.0 bar. To this process it will be referred to in the following as PROCESS 2A.

Depending on the activity of the catalyst and the reaction conditions, step a of PROCESS 2A can also proceed to the final products, the compounds of the formula VIIa, so that the compounds of the formula Ia are not isolated.

Therefore, a further aspect of the present invention is the manufacture of a compound of the formula VIIa

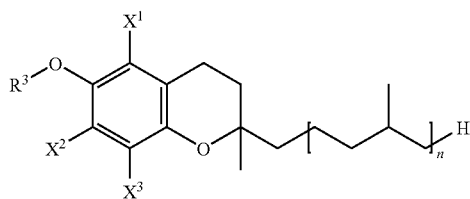

by reacting a compound of the formula IIa

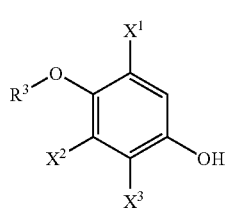

with a compound of the formula III and/or IV in an organic solvent

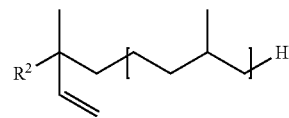

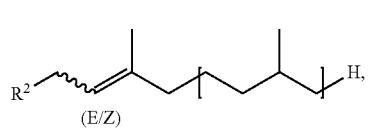
(E/Z)

with $R^2$, $R^3$, n, $X^1$, $X^2$ and $X^3$ having the same meanings and preferences as above, whereby the reaction is carried out in the presence of a Lewis acid or a mixture of a Lewis acid with a Bronsted acid as the catalyst under pressure, preferably at an absolute pressure of at least 1.1 bar, more preferably at an absolute pressure of from about 1.1 bar to about 20.0 bar, even more preferably at an absolute pressure of from about 1.1 bar to about 6.0 bar. To this process it will be referred to in the following as PROCESS 3A.

In still another aspect the invention relates to a process for the manufacture of compounds of the formula VIId (if n=3: tocyl alkanoates and tocopheryl alkanoates), especially α-tocopheryl alkanoates (formula VIId with n=3, $X^1$=$X^2$=$X^3$=methyl),

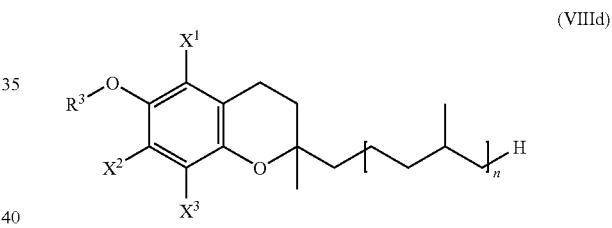

by reacting a compound of the formula VIId (if n=3: a tocol or tocopherol), especially α-tocopherol (formula VIId with n=3, $X^1$=$X^2$=$X^3$=methyl), obtained according to the process of the present invention,

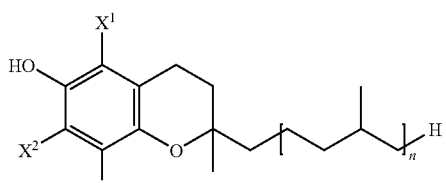

with an acylating agent. In a preferred embodiment the reaction is carried out in the presence of a Lewis acid as the catalyst. In another preferred embodiment the reaction is carried out at reduced pressure, preferably at an absolute pressure of below 0.9 bar, or under pressure, preferably at an absolute pressure of at least 1.1 bar (in the following referred to as PROCESS 5).

Concerning the symbol n: it is an integer from 0 to 3.
Concerning the symbols $X^1$, $X^2$ and $X^3$: they have the same meanings as given above.
Concerning the substituent R: it is selected from the group consisting of acetyl, propionyl, pivaloyl, $HO_2C$—$CH_2$—

CH₂—CO, nicotinoyl or benzoyl; preferably R is HO₂C—CH₂—CH₂—CO or acetyl, more preferably R is acetyl.

In a preferred aspect the invention relates to a process for the manufacture of compounds of the formula VIIIa, preferably of compounds of the formula VIIIa with n=3 (tocyl alkanoates and tocopheryl alkanoates), more preferably of α-tocopheryl alkanoates (formula VIII with n=3),

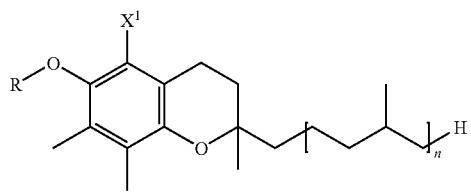
(VIII)

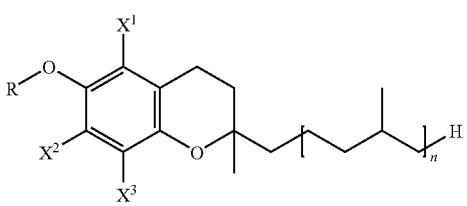
(VIIIa)

by reacting a compound of the formula VIIc, preferably a compound of the formula VIIc with n=3 (a tocol or tocopherol), more preferably α-tocopherol (formula VIIb with n=3),

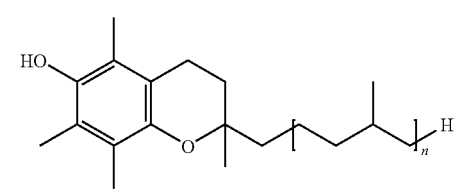
(VIIb)

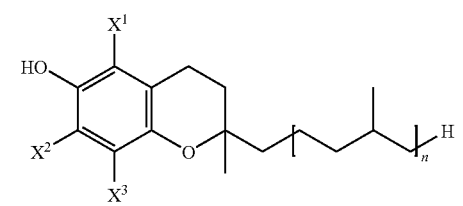
(VIIc)

with an acylating agent characterized in that the reaction is carried out in the presence of a Lewis acid as the catalyst at reduced pressure, preferably at an absolute pressure of below 0.9 bar, or under pressure, preferably at an absolute pressure of at least 1.1 bar (in the following referred to as PROCESS 5A).

Concerning the symbols n, $X^1$, $X^2$ and $X^3$: they have the same meanings as given above.

Concerning the substituent R: it is selected from the group consisting of acetyl, propionyl, pivaloyl, HO₂C—CH₂—CH₂—CO, nicotinoyl or benzoyl; preferably R is HO₂C—CH₂—CH₂—CO or acetyl, more preferably R is acetyl.

In the same way as compounds of the formula VIII and VIIIa are manufactured compounds of the formula X with $R^1$ being acetyl, propionyl, pivaloyl, HO₂C—CH₂—CH₂—CO, nicotinoyl or benzoyl, and n being an integer from 0 to 3,

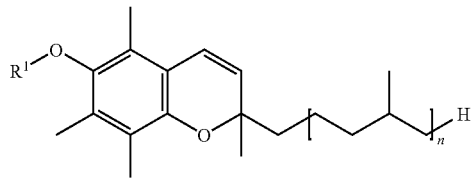
(X)

can also be manufactured by reacting a compound of the formula X with $R^1$ being hydrogen and n having the same meaning as above with an appropriate acylating agent in the presence of a Lewis acid as the catalyst at reduced pressure, preferably at an absolute pressure of below 0.9 bar, or under pressure, preferably at an absolute pressure of at least 1.1 bar. To this process, which is also an object of the present invention, it will be referred to as PROCESS 5B in the following.

While in a preferred embodiment of PROCESS 5A of the present invention chroman alkanoates of the formula VIIIa such as (all-rac)-TCPA (formula VIII with n=3; see above), especially (all-rac)-TCPAc (formula VIII with n=3 and R=acetyl) is produced, the invention is not limited to the production of that particular isomeric form and other isomeric forms can be obtained by e.g. using TCP (formula VIIb with n=3) as the starting material in the appropriate isomeric form. Thus, e.g. (R,R,R)-TCPA/TCPAc will be obtained when using (R,R,R)-TCP as starting material, since no epimerization occurs at reaction temperatures below 120° C. The same applies for the other compounds of the formula VIIc used as starting materials such as e.g. tocols and tocopherols, if n=3.

In a preferred embodiment the (all-rac)-α-tocopherol (formula VIIb with n=3) obtained by PROCESS 2 or 3 is acetylated after removal of the solvent without further purification with acetic anhydride and with total conversion, if PROCESS 2 or 3 is carried out in the presence of a Lewis acid as the catalyst. No additional catalyst needs to be used as the catalyst (Lewis acid) is still present from the reaction before. Furthermore, it is a special advantage that the reaction mixture of the manufacture of e.g. (all-rac)-α-tocopherol can be acetylated at the reaction temperature the mixture already has. When indium(III) salts are used as the catalysts, the acetylation even proceeds at room temperature in a short reaction time (up to 10 minutes). After acetylation (all-rac)-α-tocopheryl acetate was isolated in excellent yield [>99.5% based on (all-rac)-α-tocopherol].

Lewis Acids and Mixtures of Lewis Acids with Bronsted Acids

Concerning the Lewis acids and/or mixtures of Lewis acids with Bronsted acids used as the catalyst under pressure in all PROCESSES 1 to 5B:

In principle all Lewis acids and mixtures of Lewis acids with Bronsted acids known to the person skilled in the art as catalysts for the condensation reaction of TMHQ or TMHQA with IP, PH or derivatives thereof can be used. Suitable catalysts are e.g. bortrifluoride ($BF_3$), a mixture of boric acid (especially orthoboric acid) and oxalic acid, triflates and heterowolfram acids. Preferred are Lewis acids, where the radius of the metal cation varies from about 73 pm to about 90 pm, preferably from about 73 pm to about 82 pm, such as the radius of $Fe^{2+}$ (0.74 Å), $Zn^{2+}$ (0.74 Å), $In^{3+}$ (0.81 Å) and $Sc^{3+}$ (0.73 Å).

Especially suitable Lewis acids are indium(III) salts such as indium(III) halides, indium(III) trifluoromethanesulfonate (=triflate) [In(SO₃CF₃)₃; In(OTf)₃] and indium(III) bis (trifluoromethanesulfonamide) [In((NSO₂CF₃)₂)₃;

In(NTf$_2$)$_3$]; scandium(III) salts such as those described on page 5, line 14 to 21 in combination with page 6, line 23 to page 7, line 33 of EP 0 658 552 A1, e.g. scandium(III) fluorosulfonate [Sc(SO$_3$F)$_3$], scandium(III) triflate [Sc(OTf)$_3$] and scandium(III) fluorobenzenesulfonate [Sc(SO$_3$C$_6$H$_4$F)$_3$]; scandium(III) bis(trifluoromethanesulfonamide) [Sc(NTf$_2$)$_3$], scandium(III) nitrate [Sc(NO$_3$)$_3$], scandium(III) sulfate [Sc$_2$(SO$_4$)$_3$] and zinc(II) bis(trifluoromethanesulfonamide) [Zn(NTf$_2$)$_2$].

More preferred are InCl$_3$, In(OTf)$_3$ and Sc(OTf)$_3$, whereby InCl$_3$ is the most preferred one. The indium and scandium salts InCl$_3$, In(OTf)$_3$ and Sc(OTf)$_3$ are known compounds which are commercially available, InCl$_3$ e.g. from Fluka (No. 57 100), In(OTf)$_3$ and Sc(OTf)$_3$ e.g. from Aldrich (No. 442 151 and 418 218). They can be used in solid form, anhydrous or hydrated (of which InCl$_3$.4 H$_2$O is an example), as well as in solution or in suspension. For PROCESS 1 and 2 the catalyst is preferably dissolved or suspended in water. The concentration of such an aqueous solution is not critical. Furthermore, all the Lewis acids cited above tolerate acetic anhydride and other acylating agents as well as protic solvents such as acetic acid, methanol, ethanol and water. After the termination of the reaction the Lewis acids used as the catalysts can be recycled.

Especially suitable mixtures of Lewis acids with Bronsted acids are the following systems: zinc(II) compounds/hydrochloric acid, zinc(II) compounds (preferably ZnCl$_2$)/gaseous HCl and Fe(II) chloride/gaseous HCl. The Fe(II) chloride can be prepared in situ by the reaction of Fe with HCl, which therefore presents an equivalent system to the system Fe(II) chloride/gaseous HCl. Suitable zinc(II) compounds are zinc (II) salts such as ZnCl$_2$, ZnBr$_2$ as well as all zinc(II) compounds which form ZnCl$_2$ under the reaction conditions, e.g. ZnO. If the system ZnCl$_2$/hydrochloric acid or ZnCl$_2$/gaseous HCl is used, it is preferred to carry out the reaction in the presence of an amine such as disclosed in the last paragraph on page 4 and the first paragraph on page 5 of EP 0 100 471 A1, which is hereby incorporated by reference, or in the presence of an ammonium salt. Alternatively the reaction is preferably carried out by using the compound of the formula III or IV such as IP or PH having been pretreated with an amine or NH$_3$ as described in DE-OS 26 06 830.

Manufacture of the Starting Materials

The starting material TMHQAc may be obtained e.g. by selective hydrolysis of 2,3,5-trimethylhydroquinone diacetate as described in EP-A 1 239 045. 2,3,5-Trimethylhydroquinone diacetate can be prepared e.g. by the acid catalyzed rearrangement of ketoisophorone in the presence of acetic anhydride or another acetylation agent as described in EP-A 0 850 910, EP-A 0 916 642, EP-A 0 952 137 or EP-A 1 028 103.

The (iso)phytyl compounds can be produced by conventional processes known to the person skilled in the art. Phytol and its derivatives represented by the formula IV with n=3 can be used as E/Z-mixture as well as in pure E- or pure Z-form. Preferred is the use of phytol and its derivatives represented by the formula IV as E/Z-mixtures. The most preferred starting material selected from the (iso)phytyl compounds is IP.

Of course any other appropriate isomeric form of the (iso) phytol derivatives can also be used. (R,R)-phytol, (R,R,R)-isophytol, (S,R,R)-isophytol or (RS,R,R)-isophytol or an appropriate (iso)phytol derivative e.g. can be used to obtain (R,R)-PTMHQ/(R,R)-PTMHQA or (RS,R,R)-TCP/(RS,R,R)-TCPA, if TMHQ/TMHQA is used as the other component.

The other (di)(methyl)hydroquinones and compounds of the formula III and IV with n being 0, 1 or 2 can be prepared by processes known to the person skilled in the art.

Process 1, Step a of Process 2, Step a of Process 2a

As will be readily apparent, the use of the compound of the formula II with R$^1$=H (=TMHQ; =formula IIa with X$^1$, X$^2$ and X$^3$=methyl and R$^3$=hydrogen) as a reactant in this process of the present invention will result in the production of a compound of the formula I with R$^1$=H such as PTMHQ (n=3) while, when using a compound of the formula II with R$^1$=acetyl, propionyl, pivaloyl, HO$_2$C—CH$_2$—CH$_2$—CO, nicotinoyl or benzoyl (=TMHQA), especially TMHQAc, the respective compound of the formula I with R$^1$=acetyl, propionyl, pivaloyl, HO$_2$C—CH$_2$—CH$_2$—CO, nicotinoyl or benzoyl such as PTMHQA/PTMHQAc (n=3) will be obtained.

If TMHQ/TMHQA is reacted with a compound of the formula III and/or IV with n being 3 in both formulas, minor amounts of the isomers of PTMHQ/PTMHQA, (Z)- or (E)-2-(3,7,11,15-tetramethyl-hexadec-3-enyl)-3,5,6-trimethyl-hydroquinone (formula Va with R$^1$=hydrogen; see above)/ (Z)- or (E)-3-(3,7,11,15-tetramethyl-hexadec-3-enyl)-2,5,6-trimethylhydroquinone-1-alkanoate (formula Va with R$^1$=acetyl, propionyl, pivaloyl, HO$_2$C—CH$_2$—CH$_2$—CO, nicotinoyl or benzoyl; see above) and/or 2-[3-(4,8,12-trimethyl-tridecyl)-but-3-enyl]-3,5,6-trimethylhydroquinone (formula VIa with R$^1$=hydrogen; see above)/3-[3-(4,8,12-trimethyl-tridecyl)-but-3-enyl]-2,5,6-trimethylhydroquinone-1-alkanoate (formula VIa with R$^1$=acetyl, propionyl, pivaloyl, HO$_2$C—CH$_2$—CH$_2$—CO, nicotinoyl or benzoyl; see above) may be formed as by-products in PROCESS 1 as well as in STEP a of PROCESS 2 and 2A. If other compounds of the formula III and/or IV are used where n=0, 1 or 2, also minor amounts of compounds of the formula V and VI may be formed as by-products.

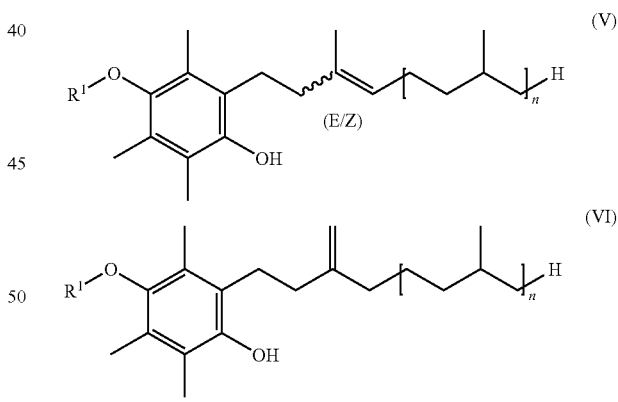

PTMHQ/PTMHQA and their isomers represented by the formulae Va and VIa (see above) are intermediates for the production of α-tocopherol or its alkanoates (final products).

Depending on the activity of the catalyst and the reaction conditions, the reaction proceeds to the final product (steps a and b of PROCESS 2) or is slowly enough so that these intermediates can be isolated (only step a of PROCESS 2 is performed). The same applies for the steps a and b of PROCESS 2a.

In a preferred embodiment of PROCESS 1 and PROCESS 2 TMHQ is reacted with PH and/or IP, more preferably with IP.

Conveniently the reaction is carried out under an inert gas atmosphere, preferably gaseous nitrogen or argon.

The reaction is preferably carried out at an absolute pressure of at least 1.1 bar, more preferably at an absolute pressure of from about 1.1 to about 20.0 bar, even more preferably at an absolute pressure of from about 1.1 bar to about 6.0 bar, even more, more preferably at an absolute pressure of from about 1.7 to about 5.1 bar, most preferably at an absolute pressure of from about 2.0 to about 3.6 bar.

The reaction temperature depends on the applied pressure and solvent because the reaction is carried out under reflux. Therefore, the reaction temperature is conveniently from about 90° C. to about 170° C., preferably from about 90° C. to about 160° C., more preferably from about 112° C. to about 160° C. and most preferably from about 125 to about 150° C.

Suitable organic solvents are aprotic non-polar organic solvents such as aliphatic hydrocarbons, halogenated aliphatic hydrocarbons, aromatic hydrocarbons, halogenated aromatic hydrocarbons and mixtures thereof.

Preferred examples of aliphatic hydrocarbons are linear, branched or cyclic $C_5$- to $C_{15}$-alkanes. Particularly preferred are linear, branched or cyclic $C_6$- to $C_{10}$-alkanes, especially preferred are hexane, heptane, octane and cyclohexane or mixtures thereof.

Preferred examples of halogenated aliphatic hydrocarbons are mono- or polyhalogenated linear, branched or cyclic $C_1$- to $C_{15}$-alkanes. Especially preferred examples are mono- or polychlorinated or -brominated linear, branched or cyclic $C_1$- to $C_{15}$-alkanes. More preferred are mono- or polychlorinated linear, branched or cyclic $C_1$- to $C_{15}$-alkanes. Most preferred are 1,1,1-trichloroethane, 1,2-dichloroethane, methylene chloride and methylene bromide.

Preferred examples of aromatic hydrocarbons are benzene, toluene, o-, m- and p-xylene, 1,2,3-trimethylbenzene, mesitylene, pseudocumene, naphthalene and mixtures thereof, particularly preferred is toluene.

Preferred examples of halogenated aromatic hydrocarbons are mono- or polyhalogenated benzene. Especially preferred are chlorobenzene, 1,2-dichlorobenzene, 1,3-dichlorobenzene and 1,4-dichlorobenzene.

The most preferred non-polar solvents differ from catalyst to catalyst:

If $InCl_3$ is used as the catalyst, toluene and heptane are the preferred solvents; especially preferred is heptane. If $Sc(OTf)_3$ is used as the catalyst, the most preferred solvent is toluene. If the catalyst system Fe $(FeCl_2)/HCl_{(g)}$ ("(g)"=gaseous) is used, the most preferred solvent is also toluene.

If the system $ZnCl_2$/hydrochloric acid or $ZnCl_2/HCl_{(g)}$ ("g"=gaseous) is used, it is more preferred to carry out process 1 or step a) of process 2/2a in the presence of an amine—such as disclosed in the last paragraph on page 4 and the first paragraph on page 5 of EP 0 100 471 A1, which is hereby incorporated by reference. The process can also be carried out by pretreating the compound of the formula III or IV such as IP or PH with an amine or $NH_3$ as described in DE-OS 26 06 830. If an amine is present in an amount of about 0.05 to about 5.0 weight%, preferably of about 0.1 to about 2.0 weight%—based on the weight of the compound III or IV, whichever is employed, the most preferred solvent for carrying out the reaction with the Zn(II) catalyst system is hexane. If no amine is present, the most preferred solvent for carrying out the reaction with the Zn(II) catalyst system is heptane. The molar ratio of the compound of the formula II or IIa (most preferred: TMHQ or TMHQA(c)) to a compound of the formula III or IV, whichever is employed, in the reaction mixture conveniently varies from about 0.95:1 to about 1:1.1, preferably from about 1:1.01 to about 1:1.05.

The amount of the aprotic non-polar organic solvent used is conveniently from about 0.1 ml to about 6.0 ml, preferably from about 0.15 ml to about 3.0 ml, based on 1 mmol of the compound of the formula III or IV, whichever is employed.

The relative amount of catalyst, based on compound III or IV, whichever is employed, is dependent on the catalyst system used and the reactants. Conveniently the relative amount of the catalyst based on compound III or IV, whichever is employed, is at least 0.01 mol%. Generally the relative amount of catalyst varies from about 0.01 to about 30 mol%. The optimal relative amount of the catalyst is different from catalyst to catalyst and also depends on the reactants:

If $InCl_3$ is used as the catalyst, it may be preferably present e.g. in a relative amount of from about 0.1 mol% to about 2.5 mol%, especially preferable in a relative amount of from about 0.1 mol% to about 2.0 mol%, more preferably in a relative amount of from about 0.1 to about 1.0 mol%, even more preferably in a relative amount of from about 0.1 to about 0.5 mol%, based on compound III or IV, whichever is employed.

If $Sc(OTf)_3$ is used as the catalyst, it may be preferably present in a relative amount of from about 0.05 mol% to about 2.0 mol%, preferably in a relative amount of from about 0.075 to about 1.5 mol%, more preferably in a relative amount of from about 0.1 to about 1.0 mol%, based on compound III or IV, whichever is employed.

If Fe and/or $FeCl_2$ in combination with HCl is used as the catalyst, it may be present in an amount as described e.g. in DE-OS 21 60 103 (page 5, end of second paragraph and claim 9) and in U.S. Pat. No. 3,789,086 (column 3, lines 27-60).

If Zn(II) and/or $ZnCl_2$ is used as the catalyst, it may be present in an amount as described e.g. in the examples 1 to 12 of U.S. Pat. No. 2,411,967, in U.S. Pat. No. 3,708,505 (page 1, right column, lines 26-44), in DE-OS 196 54 038 (page 2, lines 55-63; page 3, lines 4-6; page 3, line 60 to page 4, line 19; page 4, line 29-38), in EP-A 0 100 471 (page 7, lines 19-24), in DE-OS 26 06 830 (page 4, last two lines to page 5, first two paragraphs), in U.S. Pat. No. 4,191,692 (second column, lines 49-62).

In this context the expression "amount of catalyst" is to be understood as referring to the weight of pure Lewis acid or pure Bronsted acid present, even though the catalyst may be impure, in the form of an adduct with a solvent and/or a solution/suspension. The relative amount of the Bronsted acid depends also on the Lewis acid used and can be chosen accordingly.

The reaction can be carried out batchwise or continuously, and in general operationally in a very simple manner, for example (i) by adding the compound of the formula III or IV—as such or dissolved in the solvent, preferably as such—portionwise or continuously to a mixture of the Lewis acid, the compound of the formula IIa/II (preferred: TMHQ or TMHQA; most preferred: TMHQ or TMHQAc) and the solvent. If a catalyst system consisting of a Lewis acid and a Bronsted acid is employed, the Bronsted acid is added continuously or batchwise, preferably continuously, to the mixture of the Lewis acid, the compound of the formula IIa/II (most preferred: TMHQ or TMHQA(c)) and the solvent.

It is also possible (ii) to add subsequently the Lewis acid, preferably as such or as aqueous solution, and the compound of the formula III and/or IV—as such or dissolved in the non-polar solvent, preferably as such—to the compound of the formula IIa/II (most preferred: TMHQ or TMHQA(c)) and the solvent. The Bronsted acid is then continuously or batchwise, preferably continuously, added to this mixture.

Conveniently, the compound of the formula III or IV is added continuously to the compound of the formula IIa/II (most preferred: TMHQ or TMHQA(c)) within about 15 to about 180 minutes, preferably within about 30 to about 150 minutes, more preferably within about 45 to about 130 minutes. The Lewis acid is preferably added at once, i.e. in its full amount, to the mixture of the compound of the formula IIa/II (most preferred: TMHQ or TMHQA(c)) and the solvent.

After completion of the addition of the compound of the formula III or IV (in the non-polar solvent) the reaction mixture is suitably heated further at the reaction temperature for about 10 minutes to about 360 minutes, preferably for about 30 minutes to about 240 minutes. The working-up can be effected by procedures conventionally used in organic chemistry.

Step b of Process 2, Step b of Process 2a

As will be readily apparent, the use of a compound of the formula II or IIa with $R^1$ and $R^3$, respectively, being hydrogen such as PTMHQ or an isomer thereof as a reactant in the process of this invention will result in the preparation of a tocol or a tocopherol such as α-tocopherol while, when using a compound of the formula II with $R^1$ being acetyl, propionyl, pivaloyl, $HO_2C—CH_2—CH_2—CO$, nicotinoyl or benzoyl and n being 3 the respective tocyl alkanoate or tocopheryl alkanoate such as α-tocopheryl alkanoate will be obtained.

For the manufacture of α-tocopherol or α-tocopheryl alkanoate PTMHQ or PTMHQA and optionally one or more isomers thereof, which are obtained as minor by-products in the manufacture of PTMHQ or PTMHQA, prepared to any method known to the person skilled in the art can be used as starting material.

This ring closure can be carried out using the same catalysts under substantially the same reaction conditions as described above for the reaction of compounds of the formula II (e.g. TMHQ: formula II with $R^1$=hydrogen; or TMHQA: formula II with $R^1$=acetyl, propionyl, pivaloyl, $HO_2C—CH_2—CH_2—CO$, nicotinoyl or benzoyl) or IIa with a compound of the formula III and/or a compound of the formula IV. Therefore, in cases, where e.g. PTMHQ or PTMHQA and optionally one or more isomers thereof are produced according to STEP a, it is sufficient to simply prolong the reaction time of STEP a to realize STEP b, i.e. to prolong the reaction time for about 30 minutes to about 240 minutes, to increase the amount of catalyst and/or to increase the reaction temperature.

Processes 3 and 3a

This reaction can be carried out using the same catalysts under substantially the same reaction conditions as described above for step a) of PROCESS 2 and 2a. Depending on the kind of catalyst, the amount of catalyst and the reaction temperature the reaction stops at the intermediates of the formula Ia/I or proceeds to the end products of the formula VII/VIIa.

Process 4

This reaction can be carried out using the same catalysts under substantially the same reaction conditions as described above for step a) of PROCESS 2 and 2a. The reaction proceeds to the final product of the formula X independent from the nature of the catalyst, the amount of catalyst and the reaction temperature.

Process 5A

According to still another aspect of this invention, a compound of the formula VIIc such as e.g. α-tocopherol or γ-tocopherol, or any other tocol as described in DE-OS 21 60 103 on page 5 in the third and forth paragraph may be converted into its alkanoate (a compound of the formula VIIIa), e.g. its acetate, by treatment with an acylating agent in the presence of a Lewis acid as the catalyst at reduced pressure, preferably at an absolute pressure of below 0.9 bar, or under pressure, preferably at an absolute pressure of at least 1.1 bar.

More preferably the absolute reaction pressure varies from about 0.02 bar to about 0.9 bar (even more preferably from about 0.1 bar to about 0.9 bar, most preferably from about 0.2 bar to about 0.9 bar) and from about 1.1 bar to about 10.0 bar (even more preferably from about 1.1 bar to about 6.0 bar, even more, more preferably from about 1.1 bar to about 5.0 bar, most preferably from about 1.1 bar to about 3.0 bar).

Therefore, the invention is also directed to a process for the manufacture of tocyl alkanoates in the presence of a Lewis acid as the catalyst at reduced pressure, preferably at an absolute pressure of below 0.9 bar, or under pressure, preferably at an absolute pressure of at least 1.1 bar.

The acylation in accordance with that aspect of the invention can be carried out using acylating agents conventionally used in the acylation of tocopherols such as anhydrides or halides.

Examples of these are anhydrides or halides of alkanoic acids such as acetic acid, propionic acid, pivalic acid, succinic acid, nicotinic acid and benzoic acid. Preferably, acetic anhydride or acid chloride, especially acetic anhydride, are/is used.

The molar ratio of the compound of the formula VIIc to the acylating agent in the reaction mixture conveniently varies from about 1:1 to about 1:5, preferably from about 1:1 to about 1:3, more preferably from about 1:1.1 to about 1:2.

Suitable Lewis acids are the ones named above.

The amount of the Lewis acid used as the catalyst is based on the lesser molar amount of reactant, i.e. the compound of the formula VIIc or the acylating agent, and can be in the range of from about 0.006 mol% to about 2.0 mol%, preferably from about 0.0075 mol% to about 1.5 mol%, more preferably from about 0.01 mol% to about 1.0 mol%, in the batchwise mode of operation. For continuous operation, the amount of catalyst will be adjusted to the size of the reactor and the flow of the reactants. It will be appreciated that the determination of the appropriate figures based on the figures for batchwise operation is within normal skill. As in the other processes of the invention the Lewis acid is added at once, i.e. in its full amount. Preferably the catalyst is added as an aqueous solution or suspension.

The temperature of the acylation is dependent on the catalyst system used and the temperature the reactants (resulting from former process steps) already have. The acylation reaction can be generally carried out at temperatures from about 20 to about 200° C., preferably from about 60 to about 180° C., more preferably from about 80 to about 160° C. When indium(III) salts are used as the catalysts, the acylation reaction is preferably carried out at temperatures below 120° C., more preferably from about 15 to about 120° C., most preferably at room temperature, i.e. from about 15 to about 40° C.

The reaction can be carried out essentially in the absence of an additional organic solvent, which is preferred.

"Essentially in the absence of an additional organic solvent" in the context of the present invention means that essentially no organic solvent is present during the reaction and that no organic solvent is deliberately added. It might, however, be possible that traces of organic solvent are present in the starting materials or the catalyst as impurities. In other words, the reaction is carried out in substance; i.e. no other compound except the compound of the formula VIIc, the acylating agent and the catalyst is intendedly used for the reaction, so that at the beginning of the reaction the amount of any substance except for the starting material, the compound of the formula VIIc and the acylating agent, and except for the catalyst in the reaction mixture is $\leq 5$ weight%, preferably $\leq 3$ weight%, more preferably $\leq 0.5$ weight%, and that no further compound is added during the reaction Alternatively it is also possible to carry out the reaction in the presence of an additional organic solvent, e.g. pyridine.

The reaction is conveniently carried out under an inert gas atmosphere, preferably gaseous nitrogen or argon.

It is a particular feature of the acylation according to the present invention that when using chiral tocols and tocopherols, e.g. (enantiomeric pure) (R,R,R)-α-tocopherol, the acylation proceeds substantially without epimerization in the presence of indium(III) salts as the catalysts, and at a temperature below 120° C., e.g. from about 20° C. to about 120° C. Thus, if e.g. (R,R,R)-α-tocopherol is used as starting material for PROCESS 5A, (R,R,R)-α-tocopheryl alkanoate is obtained.

In especially preferred embodiments of PROCESS 5A α-tocopherol (formula VIIb with n=3; see above), β-tocopherol (formula VII c with $X^1=X^3=CH_3$, $X^2=H$ and n=3), γ-tocopherol (formula VII c with $X^2=X^3=CH_3$, $X^1=H$ and n=3) and δ-tocopherol (formula VII c with $X^1=X^2=H$, $X^3=CH_3$ and n=3), preferably α-tocopherol and β-tocopherol, more preferably α-tocopherol, are/is acylated to the appropriate tocopheryl alkanoates (compounds of the formula VII/VIIa with n=3 and R, $X^1$, $X^2$ and $X^3$ having the same meanings and preferences as above). More preferred the appropriate acetates are manufactured, especially with indium(III) salts (preferences see above) as the catalysts and at a temperature below 120° C., preferably at room temperature, i.e. a temperature between 15 and 40° C.

Process 5B

It can be carried out using the same catalysts under substantially the same reaction conditions as described above for PROCESS 5A.

Process for the Manufacture of Formulations of α-tocopherol or its Alkanoates

The α-tocopherol or its alkanoate obtained by one of the processes of the present invention can further be formulated by any method known to the person skilled in the art, e.g. as those disclosed in U.S. Pat. No. 6,162,474, US 2001/0009679, U.S. Pat. Nos. 6,180,130, 6,426,078, 6,030,645, 6,150,086, 6,146,825, 6,001,554, 5,938,990, 6,530,684, 6,536,940, US 2004/0053372, U.S. Pat. Nos. 5,668,183, 5,891,907, 5,350,773, 6,020,003, 6,329,423, WO 96/32949, U.S. Pat. No. 5,234,695, WO 00/27362, EP 0 664 116, US 2002/0127303, U.S. Pat. Nos. 5,478,569, 5,925,381, 6,651,898, 6,358,301, 6,444,227, WO 96/01103 and WO 98/15195.

The following Examples illustrate the invention further.

EXAMPLES

In the following examples minor amounts of the following by-products were obtained:

PTMQ: phytyltrimethylquinone:

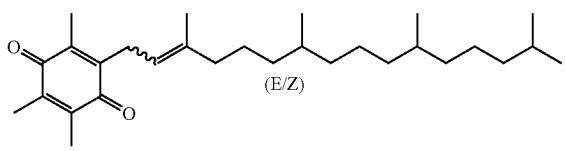 [SMILES: CC(=CCC1=C(C)C(=O)C(C)=C(C)C1=O)CCCC(C)CCCC(C)CCCC(C)C]

PTD: phytadienes=dehydrated by-products of IP (easily separable);

BZF: benzofuranes:

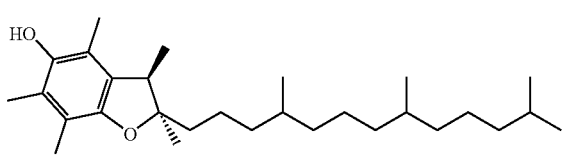

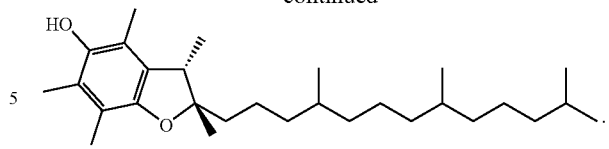

Phytyl-toluene compounds and their double-bond isomers (easily separable):

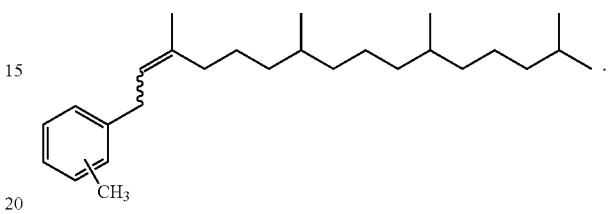

The analysis of the products was done by gas chromatography (GC) using an internal standard.

Jeffsol EC50® is a solvent mixture available from Huntsman Corp., PO Box 15730 Austin, Tex., USA/Antwerp 2030, Belgium, which consists of ethylene carbonate and propylene carbonate in the volume ratio 1:1.

If examples were carried out at "atmospheric pressure" (comparative examples), this indicates that the reaction was carried out at a pressure from about 0.96 bar to about 1.03 bar.

Examples 1-32

Processes with $InCl_3$ or $In(OTf)_3$ as the Catalyst

Examples 1-14

Preparation of PTMHQ

Examples 1-3

$InCl_3$ as the Catalyst 12.88 mmol of TMHQ and 8.58 mmol of IP were reacted in the solvent or solvent system given in Table 1 in the presence of $InCl_3$ as the catalyst (amounts of the catalyst given in Table 1) and at atmospheric pressure. The reaction time was 2 hours. For further details and the results see Table 1.

Examples 4 and 5

$In(OTf)_3$ as the Catalyst 12.88 mmol of TMHQ and 8.58 mmol of IP were reacted in a mixture of 20 ml of heptane and 20 ml of Jeffsol EC 50® in the presence of increasing amounts (see Table 1) of $In(OTf)_3$ as the catalyst and at atmospheric pressure. For further details about the reaction conditions and the results see Table 1.

TABLE 1

The amount of THMQ was 12.88 mmol in all cases,
the amount of IP was 8.58 mmol in all cases.

| Example | Catalyst | Amount of catalyst [mol %] | Solvent | Reaction temperature | Reaction time [hours] | Yield of PTMHQ [%] - based on IP |
|---------|----------|---------------------------|---------|---------------------|----------------------|----------------------------------|
| 1 | $InCl_3$ | 0.1 | 20 ml of Jeffsol EC50 ® + 20 ml of heptane | 94° C. | 2 | 47.2 |
| 2 | $InCl_3$ | 2.0 | 20 g of butyl acetate | reflux | 2 | 60.2 |
| 3 | $InCl_3$ | 2.0 | 20 g of diethylketone | reflux | 2 | 80.3 |
| 4 | $In(OTf)_3$ | 0.01 | 20 ml of Jeffsol EC50 ® + 20 ml of heptane | 94° C. | 12 | 58.7 |
| 5 | $In(OTf)_3$ | 1.0 | 20 ml of Jeffsol EC50 ® + 20 ml of heptane | 22° C. | 100.5 | 90.5 |

Examples 6 and 7

$InCl_3$ as the Catalyst

Varying amounts of TMHQ were reacted with 17.17 mmol of IP in 45 ml of toluene at 110° C. in the presence of 1.0 mol% of $InCl_3$—based on IP—as the catalyst and at atmospheric pressure. Further details and the results are presented in Table 2.

Example 8

$In(OTf)_3$ as the Catalyst

TMHQ (38.63 mmol) and IP (25.75 mmol, 97%, added during 1 hour) were reacted in a molar ratio of 1.5:1 in the presence of 1.0 mol% of $In(OTf)_3$ as the catalyst (amount based on IP) at 22° C. and at atmospheric pressure. For further details and the results see Table 2. After separation of the heptane phase and washing of the heptane phase with Jeffsol EC50® (60 ml) the resulting mixture (suspension in heptane) was filtered under vacuum. The pasty nearly colorless solid was analysed by GC.

Example 9

$In(OTf)_3$ as the Catalyst

TMHQ (24.691 g, 161.1 mmol) and IP (38.833 ml, 107.4 mmol, 97%, added during 1 hour) were reacted in a molar ratio of 1.5:1 in the presence of 1.0 mol% of $In(OTf)_3$ as the catalyst (amount based on IP) at 22° C. and at atmospheric pressure. For further details and the results see Table 2. After separation of the heptane phase and washing of the heptane phase with Jeffsol EC50® (250 ml) the resulting suspension in heptane was filtered under vacuum. The pasty nearly colorless solid was analysed by quantitative GC.

TABLE 2

The amount of catalyst was 1.0 mol % - based on IP - in all cases.

| | Example | | | |
|---|---|---|---|---|
| | 6 | 7 | 8 | 9 |
| Amount of TMHQ [mmol] | 17.17 | 25.76 | 38.63 | 161 |
| Amount of IP [mmol] | 17.17 | 17.17 | 25.75 | 107 |
| Catalyst | $InCl_3$ | $InCl_3$ | $In(OTf)_3$ | $In(OTf)_3$ |
| Solvent | Toluene | Toluene | 60 ml of Jeffsol EC50 ® + 60 ml of heptane | 250 ml of Jeffsol EC50 ® + 250 ml of heptane |
| Reaction temperature | 110° C. | 110° C. | 22° C. | 22° C. |
| Reaction time [hours] | 10 | 2 | 92 | 192 |
| Yield of PTMHQ - based on IP | 63.9 | 73.6 | 88.7 | 59.7 |

Examples 10-14

200 mmol of TMHQ were reacted with 200 mmol of IP (examples 10 and 13) and 203 mmol of IP (examples 11, 12 and 14), respectively, in the presence of increasing amounts of $In(OTf)_3$ (example 10) or $InCl_3$ (examples 11-14) as the catalyst in 100 ml of an organic solvent. Examples 10 and 14 were carried out under pressure, whereby examples 11-13 were carried out at atmospheric pressure. For the reaction temperature, the pressure, the reaction time and the type of solvent see Table 3.

TABLE 3

The amount of solvent was 100 ml in all cases. The amount of TMHQ was 200 mmol in all examples 11, 12 and 14 a molar excess of IP of 1.5 mol % based on the amount of TMHQ was used. The yield of PTMHQ is based on IP.

| Example | Amount of IP [mmol] | Catalyst and its amount [mol %] | Solvent | Reaction temperature | Pressure [bar] | Reaction time | Yield of PTMHQ [%] |
|---|---|---|---|---|---|---|---|
| 10 | 200 | 0.001 In(OTf)$_3$ | Toluene | 137° C. | 2 | 3 hours | 35.0 |
| 11 | 203 | 0.25 InCl$_3$ | Heptane | 98° C. | 1 | 4 hours | 61.2 |
| 12 | 203 | 0.5 InCl$_3$ | Heptane | 98° C. | 1 | 3 hours | 48.8 |
| 13 | 200 | 1.0 InCl$_3$ | Heptane | 98° C. | 1 | 2 hours | 43.4 |
| 14 | 203 | 2.0 InCl$_3$ | CH$_2$Cl$_2$ | 40° C. + 86° C. | 4 | 23 hours + 22 hours | 52.9 |

Examples 15-29

Preparation of (all-rac)-TCP

Examples 15-16

Preparation of (all-rac)-TCP at Atmospheric Pressure

In a 250 ml Büchi reactor or an autoclave equipped with a stirrer, a thermometer, a pressure indicator, a Dean-Stark separator, and a reflux condenser 30.447 g (200 mmol) of TMHQ (99.97%), certain amounts of InCl$_3$ (see Table 4; amounts based on IP) and 100 ml of toluene were heated at 114° C. under a continuous nitrogen flow and under an absolute pressure of 1.0 bar. 74.035 ml (200 mmol) of IP (94.6%) were added at a feed rate of 1.234 ml per minute. Approximately 3.6 ml water were collected until the end of the reaction. After completion of the addition the reaction mixture was stirred for 1 hour at 114° C. and cooled down to room temperature. The reaction mixture was concentrated under reduced pressure (45° C. at 95 to 15 mbar). (all-rac)-TCP was obtained as a viscous oil. For the results see Table 4.

Examples 17-18

Preparation of (all-rac)-TCP Under Pressure

Examples 15 and 16 were repeated, but the reaction was carried out at 137° C. under an absolute pressure of 2 bar. After 1 hour at 137° C. the reaction mixture was cooled down to room temperature and once at room temperature the pressure was released. For the results see Table 4, 5 (example 18 only) and 12 (example 18 only).

Example 19

Preparation of (all-rac)-TCP Under Pressure

In a 250 ml Büchi reactor or an autoclave equipped with a stirrer, a thermometer, a pressure indicator, a Dean-Stark separator, and a reflux condenser, 30.447 g (200 mmol) of TMHQ (99.97%,), 5 ml of InCl$_3$ (0.2 M aqueous solution, 0.5 mol%, 1 mmol) and 100 ml of heptane were heated at 147° C. under a continuous nitrogen flow and under an absolute pressure of 3.4 bar. 75.304 ml (203 mmol) of IP (94.6%) were added at a feed rate of 0.605 ml per minute. Approximately 3.6 ml water were collected until the end of the reaction. After completion of the addition the reaction mixture was stirred for 1 hour at 147° C. and cooled down to room temperature. Then the pressure was released. The reaction mixture was concentrated under reduced pressure (45° C. at 110 to 15 mbar). (all-rac)-TCP was obtained as a viscous oil (91.51 g). The yield was 92.0%—based on IP. For the results see Table 4, 6, 7, 8 and 12.

TABLE 4

Comparison between experiments at atmospheric pressure and under pressure in toluene with InCl$_3$ as the catalyst. The conversion of IP was 100% in all cases.

| Example | Catalyst | Amount of catalyst [mol %] | Solvent | Reaction temperature [° C.] | Pressure [bar] | Yield of TCP [%] = Selectivity for TCP [%] |
|---|---|---|---|---|---|---|
| 12 | InCl$_3$ | 0.5 | heptane | 98 | 1.0 | 18.5 |
| 15 | InCl$_3$ | 0.5 | toluene | 114 | 1.0 | 59.8 |
| 16 | InCl$_3$ | 2.0 | toluene | 114 | 1.0 | 90.1 |
| 17 | InCl$_3$ | 0.5 | toluene | 137 | 2.0 | 81.2 |
| 18 | InCl$_3$ | 2.0 | toluene | 137 | 2.0 | 95.7 |
| 19 | InCl$_3$ | 0.5 | heptane | 147 | 3.4 | 92.0 |

Examples 20 and 22 (*)

Preparation of (all-rac)-TCP with InCl$_3$ as the Catalyst in Different Solvents and Under Pressure 200 mmol of TMHQ and 203 mmol of IP (corresponding a molar excess of 1.38 mol%-based on the amount of TMHQ) were reacted in 100 ml of toluene at 137° C. or in 100 ml of heptane at 147° C. The IP was added during 120 minutes. Afterwards the mixture was reacted for further 60 minutes. All yields and selectivities (given in Table 5) are based on IP. See also Table 6.

Examples 21, 23 and 24

Preparation of (all-rac)-TCP with Different Amounts of Indium Salts as the Catalyst and Under Pressure 200 mmol of TMHQ and 200 mmol of IP were reacted in 100 ml of toluene at 137° C. or in 100 ml of heptane at 147° C. The IP was added during 60 minutes. Afterwards the mixture was reacted for further 60 minutes. All yields and selectivities (given in Table 5) are based on IP.

TABLE 5

Influence of the counterion of the indium salt. The amount of catalyst was 2.0 mol %, based on IP, in all cases. The conversion of IP was 100% in all cases.

| Example | Catalyst | Solvent | IP addition time [hour/s] | Pressure [bar] | Yield of TCP [%] = Selectivity for TCP [%] |
|---|---|---|---|---|---|
| 18 | InCl$_3$ | Toluene | 1 | 2.0 | 95.7 |
| 20* | InCl$_3$ | Toluene | 2 | 2.0 | 95.5 |
| 21 | InCl$_3$ | Heptane | 1 | 3.4 | 89.5 |
| 22* | InCl$_3$ | Heptane | 2 | 3.4 | 93.9 |
| 23 | In(OTf)$_3$ | Toluene | 1 | 2.0 | 72.3 |
| 24 | In(OTf)$_3$ | Heptane | 1 | 3.4 | 65.6 |

*molar excess of IP of 1.38%

With InCl$_3$ excellent yields were obtained in both solvents, heptane and toluene. The selectivity for the formation of the desired 6-membered ring product (all-rac)-TCP with this catalyst was very high compared to results with In(OTf)$_3$ as a difference of 28 to 30% for the selectivity was observed.

It was also found that in heptane a small excess of IP (+1.38 mol%) led to a much better yield (see Table 5, example 22) than carrying out the reaction with equimolar amounts of IP and TMHQ. In fact, (all-rac)-TCP could be isolated in 93.9% yield after work-up. It has to be emphasized that at atmospheric pressure a TMHQ/IP ratio of 1.5/1 had to be used whereas, under pressure, an equimolar ratio was sufficient to produce the desired chroman ring compound (all-rac)-TCP in excellent yield.

It is noteworthy that the proportion of TMHQ used for these reactions under pressure was twenty-fold higher than at atmospheric pressure (4 mol/L instead of 0.2 mol/L) and it did not affect the yield of the reaction.

Example 25

Preparation of (all-rac)-TCP with InCl$_3$ as the Catalyst and Under Pressure 200 mmol of TMHQ and 203 mmol of IP were reacted in 100 ml of toluene at 137° C. The IP was added during 120 minutes. The reaction mixture was then further reacted for another 60 minutes. The yield—based on IP—is given in Table 6. See also Table 7.

Example 26

Preparation of (all-rac)-TCP with InCl$_3$ as the Catalyst and Under Pressure 200 mmol of TMHQ and 203 mmol of IP were reacted in 100 ml of toluene at 137° C. The IP was added during 120 minutes. The reaction mixture was then reacted for further 566 minutes. The yield—based on IP—is given in Table 6.

Example 27

Preparation of (all-rac)-TCP with InCl$_3$ as the Catalyst and Under Pressure 200 mmol of TMHQ and 203 mmol of IP were reacted in 100 ml of heptane at 147° C. The IP was added during 120 minutes. The reaction mixture was then further reacted for another 120 minutes. The yield—based on IP—is given in Table 6.

TABLE 6

Influence of the amount of InCl$_3$. The conversion of IP was 100% in all cases.

| Example | Amount of InCl$_3$ [mol %] | Solvent | Pressure [bar] | Yield of TCP [%] = Selectivity for TCP [%] |
|---|---|---|---|---|
| 12 | 0.5 | Heptane | 1.0 | 18.5 |
| 19 | 0.5 | Heptane | 3.4 | 92.0 |
| 20 | 2.0 | Toluene | 2.0 | 95.5 |
| 22 | 2.0 | Heptane | 3.4 | 93.9 |
| 25 | 0.5 | Toluene | 2.0 | 90.2 |
| 26 | 0.25 | Toluene | 2.0 | 85.1 |
| 27 | 0.25 | Heptane | 3.4 | 81.5 |

When the amount of InCl$_3$ was reduced to 0.25 mol% (all-rac)-TCP was still obtained in good yield (see Table 6, examples 26 and 27). However a longer reaction time (e.g. up to 566 minutes in toluene, example 26) was needed to obtain nearly total ring closure.

It appeared that best results were obtained (selectivity (yield)) for (all-rac)-TCP using a catalyst amount of 0.5 mol% to 2% InCl$_3$, especially in heptane. In toluene and in heptane, the desired chroman product (all-rac)-TCP could be isolated in 90.2 up to 96.0% yield.

Example 28

Preparation of (all-rac)-TCP in Cyclohexane at an Absolute Pressure of 4.0 Bar 200 mmol of TMHQ and 203 mmol of IP were reacted in 100 ml of cyclohexane at 135° C. and under an absolute pressure of 4.0 bar in the presence of 0.5 mol% of InCl$_3$—based on IP. The IP was added during 120 minutes. Afterwards the mixture was reacted for further 380 minutes. The yield of (all-rac)-TCP given in Table 7 is based on IP.

Example 29

Preparation of (all-rac)-TCP in Hexane Under Pressure 200 mmol of TMHQ and 203 mmol of IP were reacted in 100 ml of hexane in the presence of 0.5 mol% of InCl$_3$—based on IP. The IP was added during 120 minutes at 125° C. and under an absolute pressure of 4.0 bar. Afterwards the mixture was reacted for further 180 minutes at 125° C. and under an absolute pressure of 4.0 bar and further 206 minutes at 135° C. and under an absolute pressure of 5.1 bar. The yield of (all-rac)-TCP given in Table 7 is based on IP.

TABLE 7

Influence of the solvent. The conversion of IP was 100% in all cases.

| Example | Solvent | Temperature of the reaction mixture | Pressure [bar] | Yield of TCP [%] = Selectivity for TCP [%] |
|---|---|---|---|---|
| 19 | Heptane | 145° C. | 3.4 | 92.0 |
| 25 | Toluene | 137° C. | 2.0 | 90.2 |
| 28 | Cyclohexane | 135° C. | 4.0 | 86.6 |
| 29 | Hexane | 125/135° C. | 4.0/5.1 | 75.1 |

One of the advantages of heptane compared to toluene was the absence of by-products such as phytyl-toluene compounds due to the solvent.

Examples 19(-a)-19-e

Reproducibility

All reactions were carried out in 100 ml of heptane with 200 mmol of TMHQ, 203 mmol of IP, 0.5 mol% of $InCl_3$ under an absolute pressure of 3.4 bar and at 147° C. IP as added within 120 minutes. The reaction time was 60 minutes. All yields are based on IP. The results are summarized in Table 8.

TABLE 8

Test of reproducibility, total conversion of IP:

| Example | Yield of TCP [%] = Selectivity for TCP [%] |
|---|---|
| 19 (-a) | 92.0 |
| 19-b | 91.8 |
| 19-c | 90.6 |
| 19-d | 92.3 |
| 19-e | 91.2 |

An excellent reproducibility was found as only a 1.04% maximum variation of the yield was observed with an average yield of 91.6% over five experiments.

Examples 30-37

Processes with $Sc(OTf)_3$ as the Catalyst

Examples 30-31

Preparation of (all-rac)-TCP with Azeotropic Removal of Water

In a Büchi reactor with a Dean-Stark separator 200 mmol of TMHQ and 200 mmol of IP were reacted in 100 ml of toluene in the presence of 0.1 mol% of $Sc(OTf)_3$—based on IP. The IP was added during 60 minutes at the temperature and at the pressure given in Table 9. Afterwards the mixture was reacted for further 60 minutes at the same temperature and pressure. The yield and selectivity of (all-rac)-TCP given in Table 9 is based on IP.

Example 32

Preparation of (all-rac)-TCP without Azeotropic Removal of Water

In an autoclave reactor 200 mmol of TMHQ and 200 mmol of IP were reacted in 100 ml of toluene in the presence of 0.1 mol% of $Sc(OTf)_3$—based on IP. The IP was added during 60 minutes at an absolute pressure of 3.6 bar and at a temperature of 140° C. Afterwards the mixture was reacted for further 60 minutes at the same temperature and pressure. The yield and selectivity of (all-rac)-TCP given in Table 9 is based on IP.

Example 33

Preparation of (all-rac)-TCP without Azeotropic Removal of Water

In a 250 ml autoclave reactor equipped with a mechanical stirrer, a thermometer and a pressure indicator 34.396 g (221 mmol) of TMHQ (98%), 1 mmol of $Sc(OTf)_3$ (0.5 mol% —based on IP) and 50 ml of toluene were heated at 140° C. under nitrogen atmosphere and under an absolute pressure of 5.6 bar. 72.350 ml (200 mmol) of IP (97%) were added at a feed rate of 2.412 ml per minute. After completion of the addition the reaction mixture was stirred for one hour at 140° C., cooled down to room temperature and when room temperature was reached the pressure was released. The reaction mixture was concentrated under reduced pressure (45° C. at 95 to 15 mbar). A viscous oil (94.76 g) was obtained and analysed by quantitative GC. The yield of (all-rac)-TCP was 81.4%—based on IP.

Examples 34 and 35

Preparation of (all-rac)-TCP with Azeotropic Removal of Water

Examples 30 and 31 were repeated, but instead of 0.1 mol% of $Sc(OTf)_3$ 1.0 mol% of $Sc(OTf)_3$ were used. The yield and selectivity of (all-rac)-TCP, based on IP, is given in Table 9.

Example 36

Example 35 was repeated but the reaction was carried out at a higher temperature and at a higher pressure. For details and the results see Table 9 and 12.

Example 37

Preparation of (all-rac)-TCP without Azeotropic Removal of Water

Example 32 was repeated, but instead of 0.1 mol% of $Sc(OTf)_3$ 1.0 mol% of $Sc(OTf)_3$ were used. The yield and selectivity of (all-rac)-TCP, based on IP, is given in Table 9.

TABLE 9

Comparison between experiments at atmospheric pressure and under pressure in toluene with $Sc(OTf)_3$ as the catalyst.

| Example | Amount of $Sc(OTf)_3$ [mol %] | Azeotropic removal of water | Pressure [bar] | Temperature of reaction mixture | Yield of TCP [%] = selectivity for TCP [%] |
|---|---|---|---|---|---|
| 30 | 0.1 | yes | 1.0 | 110° C. | 78.2 |
| 31 | 0.1 | yes | 2.0 | 137° C. | 74.5 |
| 32 | 0.1 | no | 3.6 | 140° C. | 72.6 |
| 33 | 0.5 | no | 5.6 | 140° C. | 81.4 |
| 34 | 1.0 | yes | 1.0 | 110-117° C. | 80.7 |
| 35 | 1.0 | yes | 2.0 | 137° C. | 81.6 |
| 36 | 1.0 | yes | 2.2 | 150° C. | 84.0 |
| 37 | 1.0 | no | 3.6 | 140° C. | 78.8 |

Examples 38-47

Processes with Fe/HCl as the Catalyst

Example 38

Preparation of (all-rac)-TCP in a Büchi Reactor

In a 500 ml Büchi reactor equipped with a stirrer, a thermometer, a pressure indicator, a Dean-Stark separator and a reflux condenser 91.3 g (595 mmol) of TMHQ (99.5%), 0.16 g (2.86 mmol) of iron powder and 137 g of toluene were heated to 140° C. under a continuous argon flow and under an absolute pressure of 1.9 bar. When the temperature of the reaction mixture was 140° C. hydrogen chloride was added to the reaction mixture at a feed rate of 0.333 g per minute for the next 5 hours (30 minutes of saturation, 4 hours addition of IP and 30 minutes further reaction afterwards; altogether 100 g of gaseous HCl were used during these 5 hours). After 30 minutes under hydrogen chloride flow at 136° C. and under an absolute pressure of 2.05 bar, 187.9 g (616 mmol) of IP (97.5%) were added at a feed rate of 0.78 g per minute. During the addition of IP (4 hours) the temperature of the reaction mixture increased from 136° C. to 146° C. Approximately 14 ml of aqueous phase were collected until the end of the reaction. After the addition of IP was completed the reaction mixture was stirred for further 30 minutes at 146° C., then the hydrogen chloride flow was stopped, replaced by an argon flow and the solution was cooled down to room temperature. When room temperature was reached the pressure was released. The reaction mixture was concentrated under reduced pressure (45° C. at 95 to 15 mbar). A viscous oil (270.2 g) was obtained and analysed by quantitative GC. The yield of (all-rac)-TCP was 91.5%—based on IP.

Examples 39-42

Preparation of (all-rac)-TCP Under Pressure

Example 38 was repeated with the same amounts of TMHQ, IP and Fe. The amount of HCl and the time for the addition of IP were, however, different. The pressure, under which the reaction was carried out was also slightly different in the examples 39-41. For further details and the results see Table 10 and 13 (examples 41 and 42 only).

Examples 43-46

Preparation of (all-rac)-TCP at Atmospheric Pressure

In a Büchi reactor with a Dean-Stark separator 600 mmol of TMHQ and varying amounts of IP (see Table 10) were reacted in 137 g of toluene (only example 48 and 49:171.1 g toluene) in the presence of varying amounts of iron powder and fed gaseous HCl (see Table 10). The gaseous HCl was added with a feed rate of 0.333 g per minute to the TMHQ in toluene. The mixture of TMHQ and toluene was saturated with HCl during 30 minutes before the IP was added during the time given in Table 10 and at an absolute pressure of 1.0 bar under a continuous HCl flow. After the complete addition of IP the mixture was reacted for further 30 minutes at the same temperature and pressure and the continuous HCl flow. Then the HCl flow was stopped and the reaction mixture worked-up. The yield and selectivity of (all-rac)-TCP given in Table 10 is based on IP.

Example 47

Preparation of (all-rac)-TCP Under Pressure

Example 46 was repeated but the reaction was carried out under an absolute pressure of 2.1 bar instead of 1.0 bar. Further details and the results are shown in Table 10.

TABLE 10

Comparison between experiments at atmospheric pressure (examples 43-46) and under pressure (examples 38-42 and 47) in toluene (under reflux) with Fe/HCl as the catalyst; the conversion of IP was 100% in all cases. All yields and selectivities are based on IP.

| Example | TMHQ/IP [mmol/mmol] | Amount of Fe [mol %] | HCl [$10^{-3}$ kg] | IP addition time [hour/s] | Pressure [bar] | Yield of TCP [%] = Selectivity for TCP [%] |
|---|---|---|---|---|---|---|
| 38 | 595/617 | 0.5 | 100.1 | 4 | 2.1 | 91.5 |
| 39 | 595/617 | 0.5 | 139.3 | 6 | 2.0 | 91.6 |
| 40 | 595/617 | 0.5 | 41.0 | 1 | 2.0 | 93.2 |
| 41 | 595/617 | 0.5 | 39.9 | 1 | 2.0 | 92.0 |

TABLE 10-continued

Comparison between experiments at atmospheric pressure (examples 43-46) and under pressure (examples 38-42 and 47) in toluene (under reflux) with Fe/HCl as the catalyst; the conversion of IP was 100% in all cases. All yields and selectivities are based on IP.

| Example | TMHQ/IP [mmol/mmol] | Amount of Fe [mol %] | HCl [$10^{-3}$ kg] | IP addition time [hour/s] | Pressure [bar] | Yield of TCP [%] = Selectivity for TCP [%] |
|---|---|---|---|---|---|---|
| 42 | 595/617 | 0.5 | 60.2 | 2 | 2.1 | 93.2 |
| 43 | 600/616 | 0.5 | 60.0 | 2 | 1.0 | 26.0 |
| 44 | 600/617 | 0.5 | 99.9 | 4 | 1.0 | 89.4 |
| 45 | 600/617 | 0.5 | 138.9 | 6 | 1.0 | 89.6 |
| 46 | 600/570 | 13.7 | 59.9 | 2 | 1.0 | 7.2 |
| 47 | 600/570 | 13.7 | 59.9 | 2 | 2.1 | 92.7 |

Examples 48-53

Processes with $ZnCl_2$/HCl as the Catalyst

Example 48

Preparation of (all-rac)-TCP in Heptane in the Absence of an Amine at Atmospheric Pressure 322 mmol of TMHQ and 320 mmol of IP were reacted in 163.3 g of heptane under reflux in the presence of $ZnCl_2$ and gaseous HCl as the catalyst (amounts see Table 11). The reaction was carried out at 1.0 bar. Further details and the results are given in Table 11.

Example 49

Preparation of (all-rac)-TCP in Heptane in the Absence of an Amine Under Pressure Example 48 was repeated, but the reaction carried out under an absolute pressure of 2.1 bar and not at 1.0 bar. Further details and the results are given in Table 11.

Example 50

Preparation of (all-rac)-TCP in Hexane in the Presence of an Amine Under Pressure In a 500 ml Büchi reactor equipped with a stirrer, a thermometer, a pressure indicator, a Dean-Stark separator and a reflux condenser 60 g (394 mmol) of TMHQ (99.5%), 12.5 g (91.7 mmol) of $ZnCl_2$, 1.2 g of tridecylamine and 177.7 g of hexane were heated to 92° C. under a continuous argon flow and under an absolute pressure of 2.2 bar. When the temperature of the reaction mixture had reached 92° C. gaseous hydrogen chloride was added to the reaction mixture at a feed rate of 0.035 g per minute to saturate the reaction mixture with HCl. (The HCl flow was continued during the addition of IP and the further reaction time, i.e. gaseous HCl was added during 2.5 hours.) After 30 minutes under hydrogen chlo-ride flow at 94° C. and at an absolute pressure of 2.2 bar, 122.6 g (403 mmol) of IP (97.5%) were added at a feed rate of 2.05 g per minute. During the addition of IP the temperature of the reaction mixture increased from 94° C. to 100° C. Approximately 7.4 ml of an aqueous phase were collected until the end of the reaction. After all IP was added the reaction mixture was stirred for further 60 minutes at 102° C., then the hydrogen chloride flow was stopped (A total of 5.3 g of hydrogen chloride were used during the 2.5 hours.), replaced by an argon flow and the solution was cooled down to room temperature. When room temperature was reached, the pressure was released. The reaction mixture was concentrated under reduced pressure (45° C. at 110 to 15 mbar). A viscous oil (176.88 g) was obtained and analysed by quantitative GC. The yield of (all-rac)-TCP was 94.9%—based on IP.

Example 51

Preparation of (all-rac)-TCP in Hexane in the Presence of an Amine Under Pressure Example 50 was repeated, but instead of 403 mmol of IP 404 mmol of IP were added and instead of 5.3 g of gaseous HCl 49.9 g of gaseous HCl were used. For further details and the results see Table 11.

Example 52

Preparation of (all-rac)-TCP in Hexane in the Presence of an Amine at Atmospheric Pressure Example 51 was repeated with the amounts of TMHQ, IP, $ZnCl_2$, tridecyl amine and gaseous HCl given in Table 11. The reaction, however, was not carried out at 2.2 bar, but at 1.0 bar. The results are presented in Table 11.

Example 53

Preparation of (all-rac)-TCP in Heptane in the Presence of an Amine atmospheric Pressure Example 51 was repeated with the amounts of TMHQ, IP, $ZnCl_2$, tridecyl amine and gaseous HCl given in Table 11. The reaction, however, was not carried out in hexane, but in heptane. The results are presented in Table 11 and 13.

TABLE 11

Comparison between experiments at atmospheric pressure (1.0 bar) and under pressure (2.1-2.2 bar) in heptane under reflux (examples 48, 49 and 53) or hexane under reflux (examples 50-52) with $ZnCl_2/HCl_{(g)}$ as the catalyst. IP was added during one hour in all cases. All yields and selectivities are based on IP. The conversion of IP was 100% in all cases.

| Example | TMHQ/IP [mmol/mmol] | Amount of $ZnCl_2$ [mol %] - based on IP | Tridecyl amine [$10^{-3}$ kg] | HCl [$10^{-3}$ kg] | Pressure [bar] | Yield of TCP [%] = Selectivity for TCP [%] |
|---|---|---|---|---|---|---|
| 48 | 322/320 | 18.3 | 0 | 39.9 | 1.0 | 75.9 |
| 49 | 322/320 | 18.3 | 0 | 40.0 | 2.1 | 86.6 |
| 50 | 394/403 | 22.7 | 1.2 | 5.3 | 2.2 | 94.9 |
| 51 | 394/404 | 22.7 | 1.2 | 49.9 | 2.2 | 94.1 |
| 52 | 394/402 | 22.8 | 1.2 | 50.0 | 1.0 | 77.8 |
| 53 | 394/400 | 22.8 | 1.2 | 49.9 | 2.2 | 91.0 |

Examples 18, 19-d, 23

Amount of by-Products

For these five experiments the precise analytical data concerning the by-products are given in Table 12.

TABLE 12

Detailed results and comparison of selectivity for Lewis acids as the catalyst.

| | Example | | | | |
|---|---|---|---|---|---|
| | 18 | 19-d | 23 | 34 | 36 |
| Amount of TMHQ to IP [mmol/mmol] | 200/200 | 200/203 | 200/200 | 200/200 | 200/200 |
| Catalyst | $InCl_3$ | $InCl_3$ | $In(OTf)_3$ | $Sc(OTf)_3$ | $Sc(OTf)_3$ |
| Amount of catalyst [mol %] | 2.0 | 0.5 | 2.0 | 1.0 | 1.0 |
| Solvent | toluene | heptane | toluene | toluene | toluene |
| Temperature of the reaction mixture [° C.] | 137 | 147 | 137 | 110-117 | 150 |
| Pressure [bar] | 2.0 | 3.4 | 2.0 | 1.0 | 2.2 |
| Time for the addition of IP [minutes] | 60 | 126 | 60 | 60 | 60 |
| Crude product [$10^{-3}$ kg] | 94.42 | 92.96 | 101.4 | 90.22 | 94.69 |
| Assay of DHTC according to GC [%] | 0.00 | 0.15 | 0.00 | 0.00 | 0.00 |
| Assay of BZF according to GC [%] | 0.33 | 0.31 | 7.43 | 3.83 | 2.70 |
| Assay of TCP according to GC [%] | 87.28 | 86.84 | 61.45 | 76.72 | 76.40 |
| Yield of TCP [%] | 95.7 | 93.7 | 72.3 | 80.7 | 84.0 |

As already stated, $InCl_3$ shows a higher selectivity for the formation of TCP than $In(OTf)_3$ and $Sc(OTf)_3$.

TABLE 13

Detailed results and comparison of selectivity for a mixture of Bronsted with Lewis acids as the catalyst

| | Example | | |
|---|---|---|---|
| | 41 | 42 | 53 |
| Amount of TMHQ to IP [mmol/mmol] | 595/617 | 595/617 | 394/400 |
| Catalyst | Fe + HCl | Fe + HCl | $ZnCl_2$ + HCl + tridecyl amine |
| Amount of catalyst [mol %] | 0.5 Fe | 0.5 Fe | 23.0 $ZnCl_2$ |
| Amount of gaseous HCl [g] | 39.9 | 60.2 | 49.9 |
| Solvent | toluene | toluene | heptane |
| Temperature of the reaction mixture | 135-146° C. | 137-147° C. | 106-109° C. |
| Pressure [bar] | 2.0 | 2.1 | 2.2 |
| Time for the addition of IP | 60 minutes | 120 minutes | 60 minutes |
| Crude product [$10^{-3}$ kg] | 271.2 | 270.9 | 176.69 |
| Assay of DHTC according to GC [%] | 0.54 | 0.39 | 0.05 |
| Assay of BZF according to GC [%] | 0.24 | 0.38 | 1.23 |
| Assay of TCP according to GC [%] | 90.0 | 91.3 | 88.9 |
| Yield of TCP [%] | 92.0 | 93.2 | 91.0 |

Example 54

Preparation of (all-rac)-3,4-dehydro-α-tocopherol 15.22 g (99.2 mmol) of TMHQ (99.2%), 29 mg (0.5 mmol) of iron powder and 70 ml of toluene were added to a 200 ml flask equipped like the Büchi reactor and the resulting beige suspension was stirred at 750 rounds per minute. The reaction mixture was heated to 111° C. at a constant heating rate of 2 K per minute. HCl was added at a flow rate of 33.8 ml per minute and argon was added at a flow rate of 3.5 ml per minute. After 45 minutes the reaction temperature of 111° C. had been reached and 31.01 g (102.4 mmol) of 1,2-dehydroisophytol (97.3%; from Teranol in Lalden, Switzerland) were added at a feed rate of 0.138 g per minute during 225 minutes. During the addition of the 1,2-dehydroisophytol toluene was slowly distilled off in order to keep the volume of the solution constant during all the reaction. The reaction temperature also increased from 111° C. to 157° C. After completion of the addition of 1,2-dehydro-isophytol the reaction mixture was stirred at this temperature for 45 minutes and cooled down to room temperature. When the heating was switched off, the HCl flow was stopped and replaced by a stronger argon flow. After 1 hour the temperature of the reaction mixture was 60° C. The reaction mixture was then concentrated under reduced pressure (60° C. at 300 to 18 mbar). The resulting oil was further concentrated under reduced pressure (60° C. at 0.3 to 0.1 mbar) during more than 2 hours to yield the crude product (45.6 g). A qualitative GC analysis of the crude product showed that it contained mainly TMHQ (25.6%) and (all-rac)-3,4-dehydro-α-tocopherol (21.1%). The crude product was purified by two successive column chromatographies (first with ethyl acetate/hexane=1/9 (v/v; silica gel 60 (Merck), particle size 0.063-0.2 mm) and finally with ethyl acetate/hexane=1/19 (v/v)) to yield (all-rac)-3,4-dehydro-α-tocopherol (5.23 g, GC 81.7%, 10.0% isolated yield, 44.1% yield based on conversion).

The invention claimed is:

1. A process for the alkenylation of phenols comprising 0 to 4 methyl groups, a total of 1 to 3 hydroxy groups and at least one unsubstituted position, whereby the unsubstituted position is ortho to a hydroxy group, with a compound of the formula III and/or IV

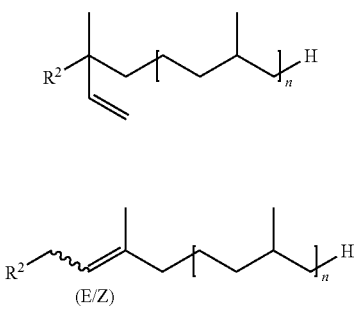

with $R^2$ being hydroxy, acetyloxy, benzoyloxy or halogen,
n being an integer from 0 to 3, and
whereby the reaction is carried out in an organic solvent in the presence of a Lewis acid or a mixture of a Lewis acid with a Bronsted acid as the catalyst at a pressure in the range of from 2 to 6 bar.

2. The process as claimed in claim 1, wherein the phenol has the formula IIa

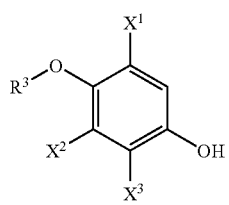

with $X^1$, $X^2$ and $X^3$ being independently from each other hydrogen or methyl and $R^3$ being hydrogen, acetyl, propionyl, pivaloyl, $HO_2C$—$CH_2$—$CH_2$—$CO$, nicotinoyl or benzoyl, with the proviso that $R^3$ is only acetyl, propionyl, pivaloyl, $HO_2C$—$CH_2$—$CH_2$—$CO$, nicotinoyl or benzoyl, if $X^1$, $X^2$ and $X^3$ are all methyl.

3. The process as claimed in claim 1, wherein the phenol has the formula II

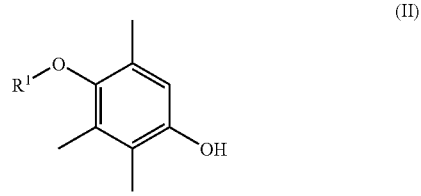

with $R^1$ being hydrogen, acetyl, propionyl, pivaloyl, $HO_2C$—$CH_2$—$CH_2$—$CO$, nicotinoyl or benzoyl.

4. A process for the manufacture of compounds of the formula VIIa

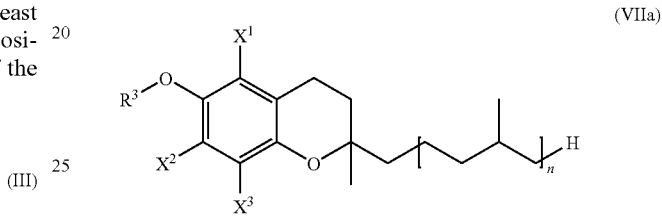

by a) (STEP a) optionally reacting a compound of the formula IIa

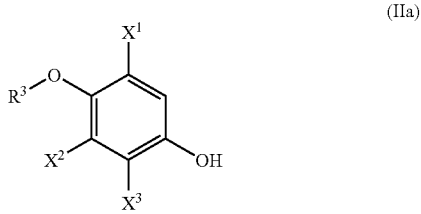

with a compound of the formula III and/or IV in an organic solvent

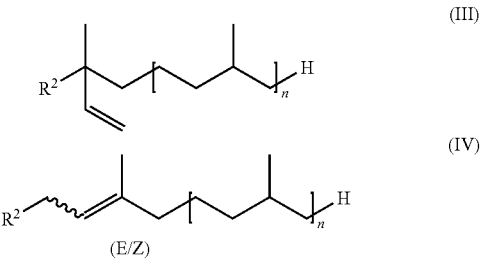

b) (STEP b) submitting in an organic solvent a compound of the formula Ia

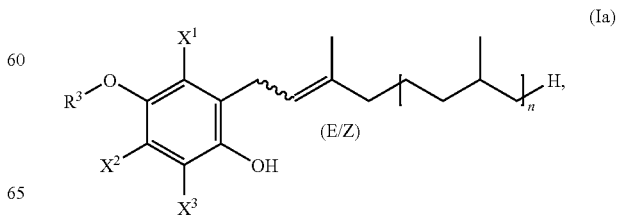

and optionally one or more double bond isomers thereof, all obtainable by step a), to ring closure to form chroman derivatives VIIa, with $R^2$ being hydroxy, acetyloxy, benzoyloxy or halogen,
$R^3$ being hydrogen, acetyl, propionyl, pivaloyl, $HO_2C-CH_2-CH_2-CO$, nicotinoyl or benzoyl,
$X^1$, $X^2$ and $X^3$ being independently from each other hydrogen or methyl,
with the proviso that $R^3$ is only acetyl, propionyl, pivaloyl, $HO_2C-CH_2-CH_2-CO$, nicotinoyl or benzoyl, if $X^1$, $X^2$ and $X^3$ are all methyl, and
n being an integer from 0 to 3,
whereby at least one of the steps a) and b) is carried out in the presence of a Lewis acid or a mixture of a Lewis acid with a Bronsted acid as the catalyst at a pressure in the range of from 2 to 6 bar.

5. A process for the manufacture of chroman derivatives VIIa

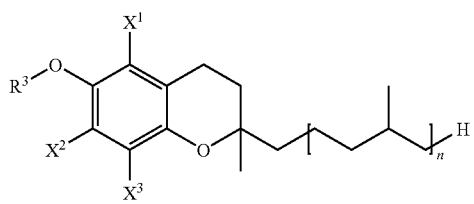

(VIIa)

by reacting of phenols comprising 0 to 4 methyl groups, a total of 1 to 3 hydroxy groups and at least one unsubstituted position, whereby the unsubstituted position is ortho to a hydroxy group, with a compound of the formula III and/or IV

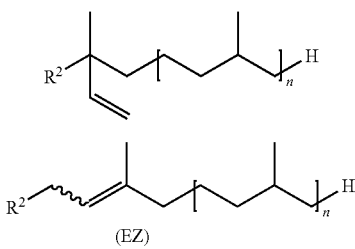

(III)

(IV)

(EZ)

with $R^2$ being hydroxy, acetyloxy, benzoyloxy or halogen, and
n being an integer from 0 to 3,
whereby the reaction is carried out in an organic solvent in the presence of a Lewis acid or a mixture of a Lewis acid with a Bronsted acid as the catalyst at greater than atmospheric pressure.

6. The process as claimed in claim 1, wherein n in formulas III and IV is 3.

7. The process as claimed in claim 1 characterized in that the Lewis acid used as the catalyst is indium trichloride, indium tribromide, indium triiodide, indium triacetate, indium tris[bis(trifluoromethanesulfonamide)], indium triflate or scandium triflate.

8. The process as claimed in claim 1 characterized in that the mixture of a Lewis acid and a Bronsted acid used as the catalyst is a mixture of $ZnCl_2$ with HCl or Fe and/or $FeCl_2$ with HCl.

9. The process according to claim 1, characterized in that the organic solvent is a non-polar aprotic organic solvent.

10. The process according to claim 9 characterized in that the non-polar aprotic organic solvent is selected from the group consisting of cyclohexane, hexane, heptane, octane, 1,1,1-trichloroethane, 1,2-dichloroethane, methylene chloride, methylene bromide, benzene, toluene, o-xylene, m-xylene, p-xylene, chlorobenzene, 1,2-dichlorobenzene, 1,3-dichlorobenzene and 1,4-dichlorobenzene.

11. A process for the manufacture of formulations of α-tocopherol, β-tocopherol, γ-tocopherol, δ-tocopherol or their alkanoates, whereby α-tocopherol, β-tocopherol, γ-tocopherol, δ-tocopherol or their alkanoates, respectively, obtained by a process according to claim 1 is used.

12. A process for the manufacture of a compound of the formula X

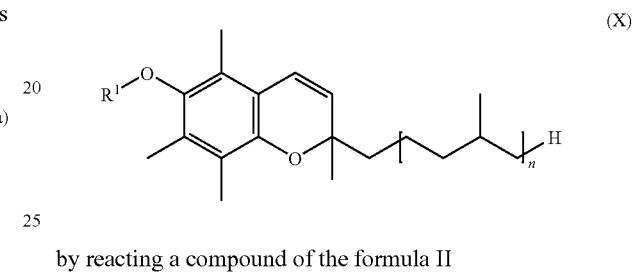

(X)

by reacting a compound of the formula II

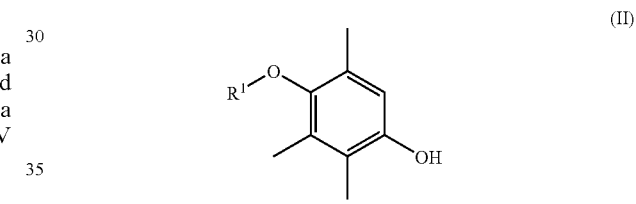

(II)

with a compound of the formula IX

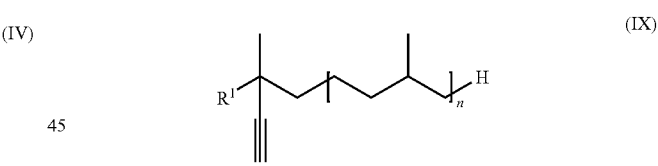

(IX)

in an organic solvent
with $R^1$ being hydrogen, acetyl, propionyl, pivaloyl, $HO_2C-CH_2-CH_2-CO$, nicotinoyl or benzoyl,
$R^2$ being hydroxy, acetyloxy, benzoyloxy or halogen,
and n being an integer from 0 to 3,
whereby the reaction is carried out in the presence of a Lewis acid or a mixture of a Lewis acid with a Bronsted acid as the catalyst at a pressure in the range of from 2 to 6 bar.

13. The process as claimed in claim 4, wherein the organic solvent is a non-polar organic solvent selected from the group consisting of aliphatic hydrocarbons, halogenated aliphatic hydrocarbons, aromatic hydrocarbons, halogenated aromatic hydrocarbons and mixtures thereof.

14. The process as claimed in claim 9, wherein the non-polar organic solvent is selected from the group consisting of aliphatic hydrocarbons, halogenated aliphatic hydrocarbons, aromatic hydrocarbons, halogenated aromatic hydrocarbons and mixtures thereof.

15. A process for the manufacture of chroman derivatives VIIa

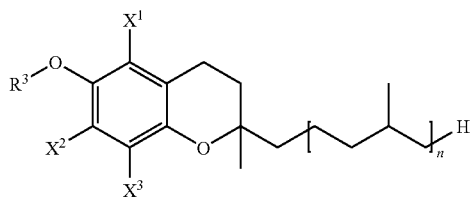

by reacting of a compound of the formula IIa

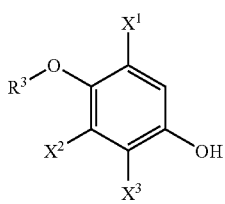

with a compound of the formula III and/or IV in an organic solvent

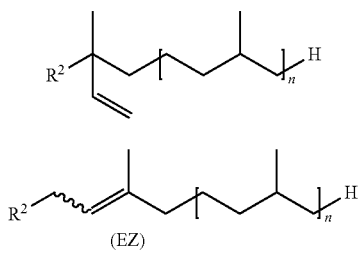

with $R^2$ being hydroxy, acetyloxy, benzoyloxy or halogen,
$R^3$ being hydrogen, acetyl, propionyl, pivaloyl, $HO_2C—CH_2—CH_2—CO$, nicotinoyl or benzoyl,
$X^1$, $X^2$ and $X^3$ being independently from each other hydrogen or methyl, with the proviso that $R^3$ is only acetyl, propionyl, pivaloyl, $HO_2C—CH_2—CH_2—CO$, nicotinoyl or benzoyl, if $X^1$, $X^2$ and $X^3$ are all methyl, and
n being an integer from 0 to 3, whereby the reaction is carried out in the presence of a Lewis acid or a mixture of a Lewis acid with a Bronsted acid as the catalyst at a pressure in the range of from 2 to 6 bar.

16. The process as claimed in claim 15, wherein the organic solvent is a non-polar organic solvent selected from the group consisting of aliphatic hydrocarbons, halogenated aliphatic hydrocarbons, aromatic hydrocarbons, halogenated aromatic hydrocarbons and mixtures thereof.

17. A process for the alkenylation of phenols comprising 0 to 4 methyl groups, a total of 1 to 3 hydroxy groups and at least one unsubstituted position, whereby the unsubstituted position is ortho to a hydroxy group, with a compound of the formula III and/or IV

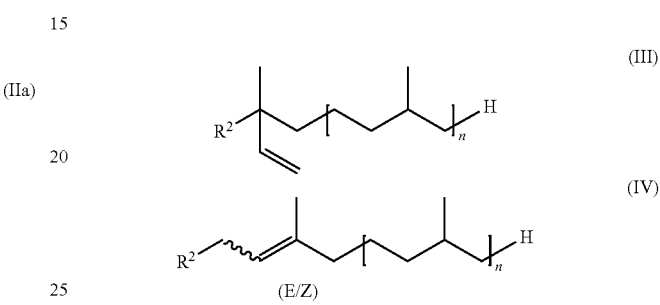

with $R^2$ being hydroxy, acetyloxy, benzoyloxy or halogen,
n being an integer from 0 to 3, and
whereby the reaction is carried out in an organic solvent in the presence of a Lewis acid or a mixture of a Lewis acid with a Bronsted acid as the catalyst at greater than atmospheric pressure, and
wherein the Lewis acid used as the catalyst is indium trichloride, indium tribromide, indium triiodide, indium triacetate, indium tris[bis(trifluoromethanesulfonamide)], indium triflate or scandium triflate.

18. The process as claimed in claim 1, wherein the process is carried out at a pressure in the range of from 2 to 3.4 bar.

19. The process as claimed in claim 4, wherein at least one of the steps a) and b) is carried out at a pressure in the range of from 2 to 3.4 bar.

20. The process according to claim 4, characterized in that all steps are carried out at a pressure in the range of from 2 to 3.4 bar.

21. The process as claimed in claim 12, wherein the process is carried out at a pressure in the range of from 2 to 3.4 bar.

22. The process as claimed in claim 15, wherein the process is carried out at a pressure in the range of from 2 to 3.4 bar.

* * * * *